(12) United States Patent
Hettrick et al.

(10) Patent No.: US 11,116,456 B2
(45) Date of Patent: Sep. 14, 2021

(54) SENSING FOR HEART FAILURE MANAGEMENT

(71) Applicant: Medtronic, Inc., Minneapolis, MN (US)

(72) Inventors: Douglas A. Hettrick, Andover, MN (US); John E. Burnes, Blaine, MN (US); Tommy D. Bennett, Shoreview, MN (US); Shantanu Sarkar, Roseville, MN (US); Eduardo N. Warman, Maple Grove, MN (US); Todd M. Zielinski, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 46 days.

(21) Appl. No.: 16/454,679

(22) Filed: Jun. 27, 2019

(65) Prior Publication Data
US 2020/0405244 A1    Dec. 31, 2020

(51) Int. Cl.
*A61B 5/00*   (2006.01)
*A61B 5/021*  (2006.01)
(Continued)

(52) U.S. Cl.
CPC ............ *A61B 5/7282* (2013.01); *A61B 5/021* (2013.01); *A61B 5/0538* (2013.01); *A61B 5/076* (2013.01);
(Continued)

(58) Field of Classification Search
CPC .............. A61N 1/36564; A61N 1/3756; A61N 1/37247; A61B 5/021; A61B 5/076;
(Continued)

(56) References Cited

U.S. PATENT DOCUMENTS

| 7,986,994 B2 | 7/2011 | Stadler et al. |
| 8,062,227 B2 | 11/2011 | Cho et al. |

(Continued)

FOREIGN PATENT DOCUMENTS

CA      2516948 A1     9/2004

OTHER PUBLICATIONS

Cowie et al., "Development and validation of an integrated diagnostic algorithm derived from parameters monitored in implantable devices for identifying patients at risk for heart failure hospitalization in ambulatory setting," European Heart Journal, vol. 34, Feb. 21, 2013, pp. 2472-2480.

(Continued)

*Primary Examiner* — Carl H Layno
*Assistant Examiner* — Anh-Khoa N Dinh
(74) *Attorney, Agent, or Firm* — Shumaker & Sieffert, P.A.

(57) ABSTRACT

In some examples, determining a heart failure status of a patient using a medical device comprising a plurality of electrodes includes determining an estimated arterial pressure waveform of the patient based on an arterial impedance signal received from at least two of the plurality of electrodes. The estimated arterial pressure waveform may comprise a plurality of arterial pressure cycles. Each of the plurality of arterial pressure cycles may correspond to a different cardiac cycle of a plurality of cardiac cycles of the patient. At least one value of an intrinsic frequency of the corresponding arterial pressure cycle may be determined for at least some of the plurality of cardiac cycles and the heart failure status of the patient may be determined based on the at least one value of the intrinsic frequency.

16 Claims, 11 Drawing Sheets

(51) Int. Cl.
    A61B 5/0295    (2006.01)
    A61B 5/053     (2021.01)
    A61B 5/0538    (2021.01)
    A61B 5/07      (2006.01)
    A61N 1/365     (2006.01)
    A61N 1/372     (2006.01)
    A61N 1/375     (2006.01)

(52) U.S. Cl.
    CPC ............ *A61B 5/486* (2013.01); *A61B 5/4836* (2013.01); *A61B 5/686* (2013.01); *A61B 5/7275* (2013.01); *A61N 1/36564* (2013.01); *A61N 1/3756* (2013.01); *A61N 1/37247* (2013.01)

(58) Field of Classification Search
    CPC ....... A61B 5/486; A61B 5/686; A61B 5/0538; A61B 5/4836; A61B 5/7275; A61B 5/7282
    See application file for complete search history.

(56)  References Cited

U.S. PATENT DOCUMENTS

| | | | |
|---|---|---|---|
| 8,241,222 | B2 | 8/2012 | Zielinski et al. |
| 8,690,787 | B2 | 4/2014 | Blomqvist et al. |
| 8,700,162 | B2 | 4/2014 | Georgakopoulos et al. |
| 8,938,292 | B2 | 1/2015 | Hettrick et al. |
| 9,026,193 | B2 | 5/2015 | Pahlevan et al. |
| 9,675,270 | B2 | 6/2017 | Sarkar |
| 2004/0167410 | A1 | 8/2004 | Hettrick |
| 2011/0125208 | A1 | 5/2011 | Karst et al. |
| 2011/0224748 | A1* | 9/2011 | Lippert ............ G16H 40/63 607/7 |
| 2012/0253207 | A1 | 10/2012 | Sarkar et al. |
| 2014/0275925 | A1* | 9/2014 | Thakur ............ A61B 5/02108 600/377 |
| 2014/0276928 | A1 | 9/2014 | Vanderpool et al. |
| 2015/0230722 | A1 | 8/2015 | Sarkar et al. |
| 2016/0256687 | A1* | 9/2016 | Baru ............ A61N 1/36114 |
| 2017/0258343 | A1* | 9/2017 | Pahlevan ............ A61B 5/02405 |

OTHER PUBLICATIONS

Narayan et al., "Central Aortic Reservoir-Wave Analysis Improves Prediction of Cardiovascular Events in Elderly Hypertensives," Hypertension (accessed from http://hyper.ahajournals.org), vol. 65, Mar. 2015, pp. 629-635.

Pahlevan et al., "Intrinsic frequency for a systems approach to haemodynamic waveform analysis with clinical applications," J. R. Soc. Interface, vol. 11, Jun. 17, 2014, 10 pp.

Shimizu et al., "Role of the augmentation index in hypertension," Therapeutic Advances in Cardiovascular Disease ( accessed from http://tac.sagepub.com), Feb. 2008, pp. 25-35.

International Search Report and Written Opinion of International Application No. PCT/US2020/036579 dated Sep. 14, 2020, 10 pp.

Tavallali et al., "Intrinsic Frequency Analysis and Fast Algorithms," Scientific Reports, vol. 8, No. 1, Mar. 20, 2018, 14 pp.

* cited by examiner

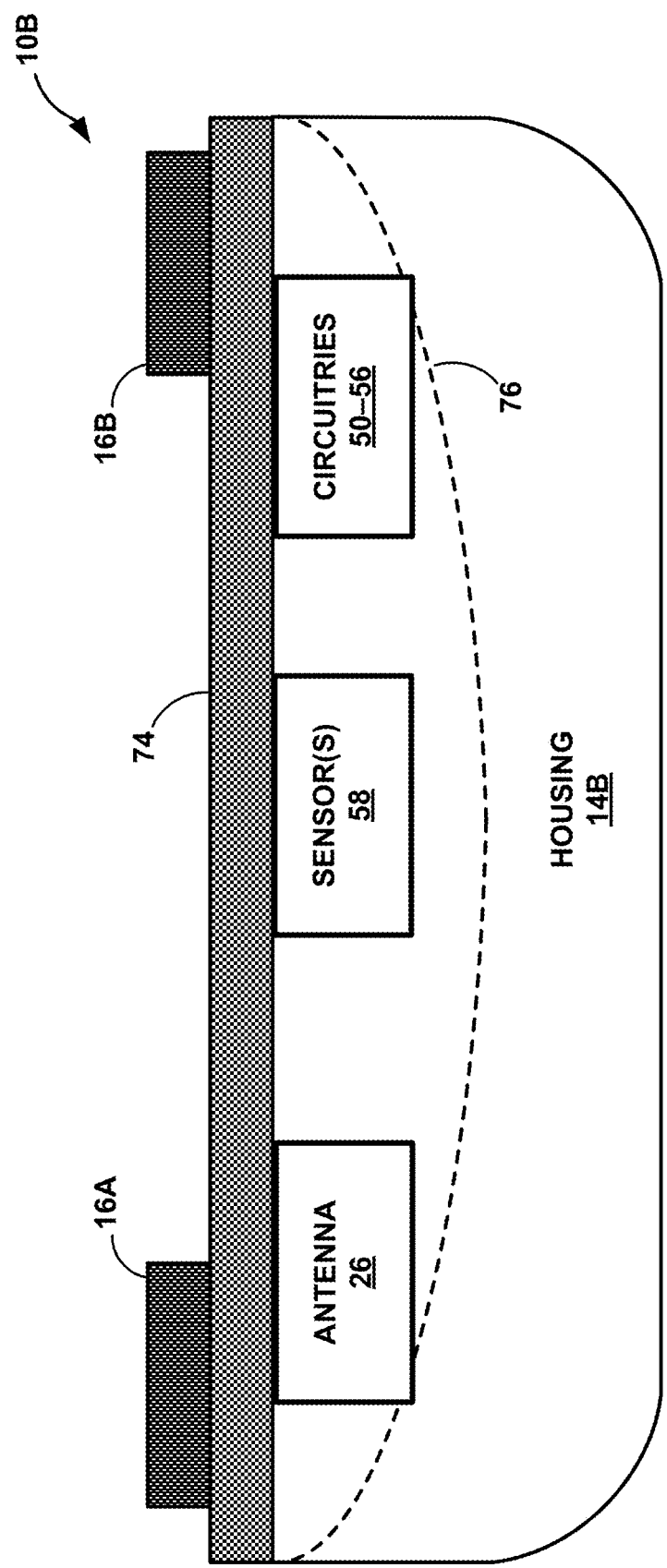

SENSING FOR HEART FAILURE MANAGEMENT

This disclosure relates generally to medical device systems, and, more particularly, medical device systems configured to monitor patient parameters.

BACKGROUND

Some types of medical devices may be used to monitor one or more physiological parameters of a patient, such as physiological parameters associated with cardiac function. Such medical devices may include, or may be part of a system that includes, sensors that detect signals associated with such physiological parameters, e.g., blood pressure parameters. Values determined based on such signals may be used to assist in detecting changes in medical conditions, in evaluating the efficacy of a therapy, or in generally evaluating patient health.

Medical devices that monitor physiological parameters related to a medical condition of a patient may evaluate values associated with the physiological parameters, such as to determine whether the values exceed a threshold or have changed over time. Values that exceed a threshold or that have changed may indicate that a patient's medical condition has deteriorated or otherwise changed, or that a therapy being administered to the patient is or is not effectively managing the patient's medical condition.

SUMMARY

In general, this disclosure is directed to techniques for determining a heart failure status of a patient, such as a patient diagnosed with a heart failure condition. Such techniques may include performing assessments associated with aspects of a patient's cardiac function, such as determining at least one value of an intrinsic frequency of an estimated arterial pressure waveform of the patient, and determining the heart failure status of the patient based on the outcome of the assessments. Ongoing monitoring of aspects of the patient's cardiac function associated with a patient's condition (e.g., heart failure condition) may enable detection of changes in cardiac function before such changes lead to symptoms, acute decompensation, hospitalization and/or the progression or development of one or more medical conditions.

The morphometry of the estimated arterial pressure waveform may contain information about one or more parameters of cardiovascular function, such as ventricular function, afterload, wave reflection, or ventricular-arterial mechanical coupling. Techniques for monitoring one or more such parameters and tracking changes therein may help improve clinical outcomes in patients who have or are at risk of developing one or more cardiovascular conditions such as hypertension, arrhythmias and/or heart failure.

Some example techniques may include determining, by a medical device system including at least one medical device, a heart failure status of a patient based on an intrinsic frequency of an estimated arterial pressure waveform of the patient. Such techniques may enable derivation of quantitative information regarding one or more parameters of cardiovascular function from at least one value of an intrinsic frequency of the estimated arterial pressure waveform of the patient. Values of one or more intrinsic frequencies of an estimated arterial pressure waveform may vary over time with variations in the morphometry of the estimated arterial pressure waveform and may be associated with one or more corresponding parameters of cardiovascular function. Thus, one or more values of one or more corresponding intrinsic frequencies of an estimated arterial pressure waveform may be used in determining the heart failure status of the patient.

An estimated arterial pressure waveform of the patient may be determined based on one or more signals received from electrodes of a medical device. For example, an estimated arterial pressure waveform of the patient may be determined based on an arterial impedance signal received from at least two of a plurality of electrodes of the medical device, such as by processing (e.g., filtering) the arterial impedance signal to identify one or more components of the arterial impedance signal that vary with arterial pressure. In this manner, the morphometry of the processed arterial impedance signal may estimate the morphometry of a corresponding arterial pressure signal, and the processed arterial impedance signal may be referred to as an estimated arterial pressure waveform. The estimated arterial pressure waveform may include a plurality of arterial pressure cycles, which may be identified from the one or more components of the arterial impedance signal from which the estimated arterial pressure waveform is identified. Each of the arterial pressure cycles may correspond to a different cardiac cycle of a plurality of cardiac cycles of the patient.

In such examples, at least one value of an intrinsic frequency of a corresponding arterial pressure cycle may be determined for at least some of the plurality of cardiac cycles. A value of the intrinsic frequency may be a value of a dominant frequency of a portion of an arterial pressure cycle around which an instantaneous frequency of the portion of the corresponding arterial pressure cycle oscillates (e.g., during a cardiac cycle). A determined value of an intrinsic frequency or a value of a relationship between multiple values of at least one intrinsic frequency that is not within a corresponding range may be indicative of a developing or worsening heart failure condition. Thus, such techniques may include determining whether a difference between a value of an intrinsic frequency and/or a relationship between multiple values of at least one intrinsic frequency satisfies one or more intrinsic frequency threshold values and/or one or more intrinsic frequency relationship threshold values. Any such techniques for determining the heart failure status of the patient may include determining the heart failure status, or more generally, a health status of the patient, based on one or more other physiological parameters indicative of heart failure status in combination with intrinsic frequency of an arterial pressure cycle, such as a tissue impedance parameter or other physiological parameter.

Determining the heart failure status of the patient further may include determining a possibility that the patient will experience an adverse medical event (e.g., worsening heart failure for which medical intervention may be beneficial) and/or transmitting the heart failure status of the patient to a remote computer for review by a clinician, other medical personal or another caregiver, or other user. Determining the possibility that the patient will experience an adverse medical event may include determining a possibility of acute decompensated heart failure or other cardiovascular event such as myocardial infarction, stroke, acute renal failure, or other adverse medical event.

In some other techniques, a clinician may determine the patient's heart failure status based on results of diagnostic or other evaluative procedures carried out during a clinician visit and prescribe treatment accordingly. For example, the clinician may prescribe medication and/or determine patient-specific values of one or more parameters at which a medical device may deliver electrical stimulation therapy (e.g., anti-arrhythmia pacing, cardiac resynchronization therapy (CRT), and/or other types of electrical stimulation therapy) to the patient's heart. However, the patient's treatment needs may change between clinician visits as the patient's heart-failure condition progresses or otherwise changes. Thus, ongoing monitoring of at least one value of an intrinsic frequency of an estimated arterial pressure waveform of the patient between clinician visits may enable early detection of changes in cardiac function before the changes lead to an adverse medical event such as recurrent symptoms, acute decompensation, and/or the progression or the patient's heart failure condition or development of one or more additional medical conditions.

Moreover, some other techniques that include deriving quantitative information regarding one or more parameters of cardiovascular function contained in the morphometry of an arterial pressure waveform may require calibration of an arterial pressure signal and/or combination of the arterial pressure signal with a simultaneously-derived flow signal. Techniques that enable derivation of quantitative information regarding one or more such parameters of cardiovascular function without necessarily performing calibration of an arterial pressure signal and/or combination with a simultaneously-derived flow signal, such as those based on identification of changes in parameters over time rather than absolute values of parameters, may simplify techniques for deriving such information, which in turn may reduce the time, complexity, and/or possibility of error involved in such deriving such information. Even in some other techniques that include deriving quantitative information regarding one or more parameters of cardiovascular function contained in the morphometry of an arterial pressure waveform that do not necessarily require calibration of an arterial pressure signal and/or combination of the arterial pressure signal with a simultaneously-derived flow signal, such techniques may be reliant directly detecting an arterial pressure waveform, such as via one or more sensors configured to detect optical, ultrasound, and/or tonometric signals. Such sensors may add to the complexity and/or cost of devices that use other types of sensors (e.g., electrodes) to detect signals associated with other physiological parameters, or may limit the utility of devices that only include sensors configured to directly detect an estimated arterial pressure waveform.

Consequently, clinical outcomes may benefit from methods for determining a heart failure status of a patient based on values of at least one intrinsic frequency of an arterial pressure cycles of an estimated arterial pressure waveform of the patient determined based on an arterial impedance signal of the patient between clinician visits. For example, such methods may enable determination of values of at least one intrinsic frequency of the arterial pressure cycles without necessarily performing calibration of an arterial pressure signal and/or combination with a simultaneously-derived flow signal. In turn, such methods may enable streamlined early detection of heart failure progression and/or prediction of a possibility of hospitalization or other medical event. In response to such information, a patient's treatment may be adjusted, e.g., by modifying a drug regimen, modifying values of one or more parameters at which a medical device may deliver electrical stimulation therapy and/or one or more values of parameters at which a left ventricular assist device (LVAD) operates, such as pump speed. Prompt adjustment of one or more aspects of a patient's heart failure treatment as the patient's heart failure condition changes may help reduce the patient's possibility of acute decompensation, hospitalization, or development of additional medical conditions.

Additionally, or alternatively, methods for determining a heart failure status of a patient based on values of at least one intrinsic frequency of an arterial pressure cycles of an estimated arterial pressure waveform of the patient determined based on an arterial impedance signal of the patient may detect the arterial impedance signal via electrodes already included in a medical device. Such electrodes may be usable for one or more other purposes, such as electrodes usable for cardiac electrogram sensing and/or delivering cardiac pacing or other therapy. Thus, the example techniques for determining a heart failure status of the patient described herein may enable use of simpler, multi-function medical devices relative to other medical devices that may rely on sensors other than electrodes to detect an estimated arterial pressure waveform of the patient.

Accordingly, techniques described herein may enable periodic determination of a heart failure status of a patient between clinician visits. In some techniques described herein, a medical device system that includes a medical device may determine a patient's heart failure status and transmit the heart failure status to a remote computer or other device external to the patient. In some cases, the patient's heart failure status may indicate the patient's possibility of acute decompensation or hospitalization based on the heart failure. The remote computer then may transmit instructions for a medical intervention (e.g., instructions for changes to a drug regimen), to a user device used by the patient, a clinician, other medical personnel, or another caregiver. In this manner, a patient's diagnoses and/or treatment for a heart failure condition may be modified as needed in between clinic visits, which may help avoid adverse medical events such as recurrent symptoms or hospitalization.

One example is a method for determining a heart failure status of a patient using a medical device comprising a plurality of electrodes. The method comprises, by processing circuitry of a medical device system comprising the medical device determining an estimated arterial pressure waveform of the patient based on an arterial impedance signal received from at least two of the plurality of electrodes, wherein the estimated arterial pressure waveform comprises a plurality of arterial pressure cycles and wherein each of the plurality of arterial pressure cycles corresponds to a different cardiac cycle of a plurality of cardiac cycles of the patient. The method further comprises, by the processing circuitry, determining, for at least some of the plurality of cardiac cycles, at least one value of an intrinsic frequency of the corresponding arterial pressure cycle, and determining the heart failure status of the patient based on the at least one value of the intrinsic frequency.

In another example, a system for determining a heart failure status of a patient using a medical device comprising a plurality of electrodes comprises the medical device, wherein the medical device comprises one or more sensors, and processing circuitry. The processing circuitry is configured to determine an estimated arterial pressure waveform of the patient based on an arterial impedance signal received from at least two of the plurality of electrodes, wherein the estimated arterial pressure waveform comprises a plurality of arterial pressure cycles and wherein each of the plurality of arterial pressure cycles corresponds to a different cardiac cycle of a plurality of cardiac cycles of the patient. The processing circuitry is further configured to determine, for at least some of the plurality of cardiac cycles, at least one value of an intrinsic frequency of the corresponding arterial pressure cycle, and determine the heart failure status of the patient based on the at least one value of the intrinsic frequency.

In another example, a non-transitory computer-readable medium stores instructions for causing processing circuitry to perform a method for determining a heart failure status of a patient using a medical device comprising a plurality of electrodes. The method comprises, by processing circuitry of a medical device system comprising the medical device determining an estimated arterial pressure waveform of the patient based on an arterial impedance signal received from at least two of the plurality of electrodes, wherein the estimated arterial pressure waveform comprises a plurality of arterial pressure cycles and wherein each of the plurality of arterial pressure cycles corresponds to a different cardiac cycle of a plurality of cardiac cycles of the patient. The method further comprises, by the processing circuitry, determining, for at least some of the plurality of cardiac cycles, at least one value of an intrinsic frequency of the corresponding arterial pressure cycle, and determining the heart failure status of the patient based on the at least one value of the intrinsic frequency.

Another example is a system for determining a heart failure status of a patient using an implantable medical device comprising a plurality of electrodes. The system comprises the implantable medical device, and processing circuitry. The processing circuitry is configured to determine an estimated arterial pressure waveform of the patient based on an arterial impedance signal received from at least two of the plurality of electrodes, wherein the estimated arterial pressure waveform comprises a plurality of arterial pressure cycles and wherein each of the plurality of arterial pressure cycles corresponds to a different cardiac cycle of a plurality of cardiac cycles of the patient. The processing circuitry is further configured to determine, for at least some of the plurality of cardiac cycles: a value of a first intrinsic frequency of a first portion of the corresponding arterial pressure cycle; and a value of a second intrinsic frequency of a second portion of the corresponding arterial pressure cycle that is subsequent to the first portion of the corresponding arterial pressure cycle. The processing circuitry is further configured to determine at least one of a difference between the value of the first intrinsic frequency and the value of the second intrinsic frequency or a ratio of the value of the first intrinsic frequency to the value of the second intrinsic frequency, compare the at least one of the difference between the value of the first intrinsic frequency and the value of the second intrinsic frequency or the ratio of the value of the first intrinsic frequency to the value of the second intrinsic frequency to at least one corresponding threshold difference value or threshold ratio value, determine the heart failure status based on the comparison, and transmit the heart failure status of the patient to a remote computer. The system further comprises the remote computer, wherein the remote computer comprises processing circuitry configured to receive the heart failure status of the patient transmitted by the processing circuitry of the implantable medical device, and transmit the instructions for the medical intervention to a user interface.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below. Other features, objects, and advantages of this disclosure will be apparent from the description and drawings, and from the claims.

BRIEF DESCRIPTION OF THE DRAWINGS

FIGS. 4A and 4B are block diagrams illustrating other example leadless implantable medical devices similar to the implantable medical device of FIG. 1;

DETAILED DESCRIPTION

Figure 1:
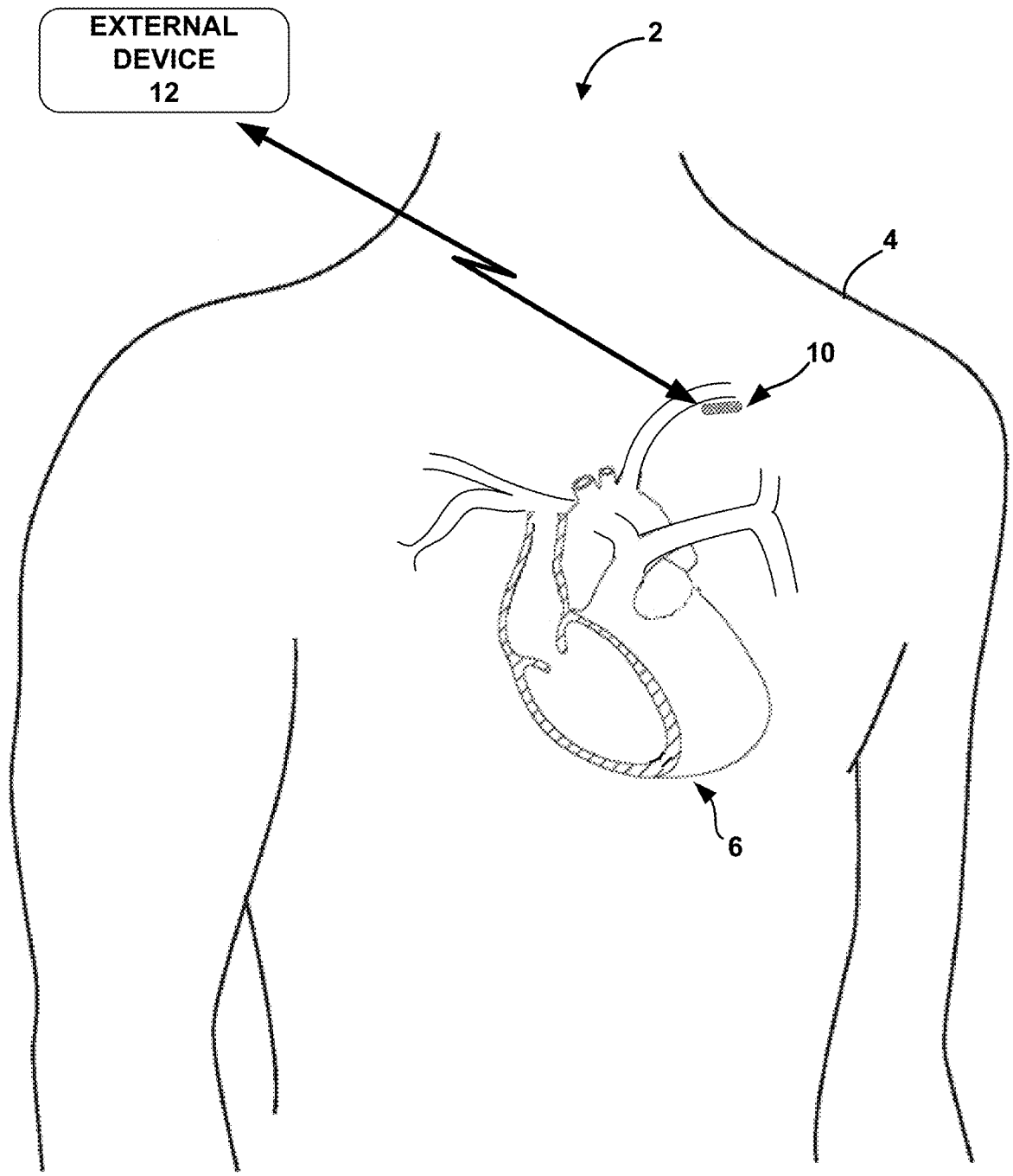
FIG. 1 is a conceptual drawing illustrating an example of a medical device system including a leadless implantable medical device and an external device in conjunction with a patient.

In general, this disclosure describes example techniques and systems related to determining a heart failure status of a patient based on at least one value of an intrinsic frequency of a pressure cycle of an estimated arterial pressure waveform that is associated with cardiac function of the patient and determined based on an arterial impedance signal. Processing circuitry of a medical device comprising a plurality of electrodes, or a system that includes the medical device, may determine an estimated arterial pressure waveform of the patient based on an arterial impedance signal received from at least two of the plurality of electrodes. For example, the processing circuitry may determine the estimated arterial pressure waveform by processing (e.g., filtering) the arterial impedance signal to identify one or more components of the arterial impedance signal that vary with arterial pressure, such as an intrinsic frequency of the estimated arterial pressure waveform. The estimated arterial pressure waveform may include a plurality of arterial pressure cycles and each of the plurality of arterial pressure cycles may correspond to a different cardiac cycle of a plurality of cardiac cycles of the patient. As described herein, one or more values of an intrinsic frequency of an arterial pressure cycle and/or a relationship between values of intrinsic frequencies of different portions of an arterial pressure cycle may be associated with a heart failure status of the patient.

After determining the estimated arterial pressure waveform of the patient based on the arterial impedance signal, the processing circuitry may determine, for at least some of the plurality of cardiac cycles, at least one value of an intrinsic frequency of the corresponding arterial pressure cycle. The processing circuitry then may determine the heart failure status of the patient based on the at least one value of the intrinsic frequency. For example, as further discussed below with respect to several example techniques, the processing circuitry may determine the heart failure status of the patient based on a comparison of a relationship between multiple values intrinsic frequencies of corresponding multiple portions of an arterial pressure cycle and/or based on a comparison of a value of the intrinsic frequency of an arterial pressure cycle to a corresponding baseline value of the intrinsic frequency.

In some example techniques, the processing circuitry may determine least one value of an intrinsic frequency of a corresponding arterial pressure cycle by determining a value of a first intrinsic frequency of a first portion of the corresponding arterial pressure cycle and a value of a second intrinsic frequency of a second portion of the corresponding arterial pressure cycle. The second portion of the arterial pressure cycle may be subsequent to the first portion of the corresponding arterial pressure cycle. For example, the first portion of the corresponding arterial pressure cycle may occur prior to a dicrotic notch of the corresponding arterial pressure cycle and the second portion of the corresponding arterial pressure cycle may occur subsequent to the dicrotic notch of the corresponding arterial pressure cycle.

Such first and second portions of an arterial pressure cycle may correspond to different events or phases of the corresponding cardiac cycle. For example, a portion of an arterial pressure cycle occurring prior to a dicrotic notch of the arterial pressure cycle may correspond to a portion of the cardiac cycle occurring prior to onset of aortic valve closure while the left ventricle and the aorta are fluidically coupled, such as during the ejection phase of the cardiac cycle when the left ventricle interacts mechanically with the arterial system. A portion of the arterial pressure cycle occurring subsequent to the dicrotic notch may correspond to a portion of the cardiac cycle occurring subsequent to onset of aortic valve closure as and/or after the left ventricle and the aorta are fluidically de-coupled. Values of the intrinsic frequencies of such first and second portions of an arterial pressure cycle vary with changes in cardiac output and inotropic state. Thus, such intrinsic frequencies may be monitored to track changes in cardiovascular function of the patient over time.

In any such examples, the processing circuitry then may determine the heart failure status of the patient based on the value of the first intrinsic frequency and the value of the second intrinsic frequency, such as based on a comparison of the value of the first intrinsic frequency to the value of the second intrinsic frequency. For example, the processing circuitry may compare the value of the first intrinsic frequency to the value of the second intrinsic frequency by determining a relationship between the value of the first intrinsic frequency and the value of the second intrinsic frequency. A relationship between the value of the first intrinsic frequency and the value of the second intrinsic frequency value, such as a difference or a ratio, may be indicative of the heart failure status of the patient. Thus, in such examples, the processing circuitry may determine the heart failure status of the patient by comparing the value of the first intrinsic frequency and the value of the second intrinsic frequency to determine a relationship therebetween. For example, the processing circuitry may determine a difference between the value of the first intrinsic frequency and the value of the second intrinsic frequency and/or a ratio of the value of the first intrinsic frequency to the value of the second intrinsic frequency, although any other suitable relationship between the value of the first frequency and the value of the second frequency may be used.

In any such example techniques, the processing circuitry then may determine the heart failure status of the patient based on the at least one of the difference between the value of the first intrinsic frequency and the value of the second intrinsic frequency or a ratio of the value of the first intrinsic frequency to the value of the second intrinsic frequency by determining whether the at least one of the difference or the ratio satisfies at least one corresponding intrinsic frequency difference threshold value or intrinsic frequency ratio threshold value that is associated with a change in the heart failure status of the patient. The processing circuitry may determine the threshold difference or ratio based on one or more values of the difference or ratio determined in the past.

An intrinsic frequency difference or ratio threshold value may be associated with a lower or a higher end of an intrinsic frequency difference or ratio range. Such a range may represent a range of values of such a difference or ratio are associated with a baseline heart failure status of the patient, e.g., a state in which a heart failure condition of the patient is adequately compensated and/or stable. A value of a difference or a ratio near the lower end of such a range may be associated with a different heart failure status of the patient than a value near the higher end of such a range. In some examples, a value of the difference between the value of the first intrinsic frequency and the value of the second intrinsic frequency that satisfies a threshold value associated with a higher end of an intrinsic frequency difference range may be indicative of worsening heart failure. For example, values of a second portion of an arterial pressure cycle occurring subsequent to a dicrotic notch of the arterial pressure cycle may decrease as arterial stiffness, hypertension, and/or other indicators of worsening heart failure increase. Values of a first portion of the arterial pressure cycle occurring prior to the dicrotic notch may remain the same or increase with a decrease in the value of the second intrinsic frequency. Thus, an increase in the value of the difference between the value of the first intrinsic frequency and the value of the second intrinsic frequency, or a decrease in the value of the ratio of the value of the first intrinsic frequency to the value of the second intrinsic frequency, may be indicative of worsening heart failure of the patient.

In some other examples, in addition to or instead of determining a heart failure status of the patient based on a comparison of the value of the first intrinsic frequency to the value of the second intrinsic frequency, the processing circuitry may determine a heart failure status of a patient by comparing at least one current value of an intrinsic frequency of an arterial pressure cycle to at least one corresponding baseline value of the intrinsic frequency and determining the heart failure status of the patient based on the comparison. In some such examples, the processing circuitry may compare the at least one current value of the intrinsic frequency to the corresponding at least one baseline value of the intrinsic frequency by determining a difference between the at least one current value of the intrinsic frequency and the corresponding at least one baseline value and determining whether the difference satisfies at least one corresponding intrinsic frequency threshold value that is associated with a change in the heart failure status of the patient.

In such examples, the at least one current value of the intrinsic frequency may be a current value of a first intrinsic frequency of a first portion of an arterial pressure cycle (e.g., a portion occurring prior to a dicrotic notch of the arterial pressure cycle) and/or a current value of a second intrinsic frequency of a second portion of the arterial pressure cycle (e.g., a portion occurring subsequent to the dicrotic notch). In some examples the at least one current value of the intrinsic frequency may be a value of a comparison between the first and second intrinsic frequency values as described herein. Such techniques may be used, for example, to monitor changes in an absolute value of the intrinsic frequency. In some examples, monitoring changes in an absolute value of one or more current values of an intrinsic frequency of an arterial pressure cycle during a period of time, such as hours, days, or any other suitable period, may enable monitoring of different aspects of a heart failure status of the patient relative to monitoring changes in a relationship between values of a first value of a first intrinsic frequency and a second value of a second intrinsic frequency. Other aspects of such example techniques may be substantially similar to corresponding aspects of example techniques in which the processing circuitry is configured to determine the heart failure status of the patient based on the difference between the first value of the first intrinsic frequency and the second value of the second intrinsic frequency.

In any of the example techniques described above, a threshold value may be a patient-specific threshold value. Additionally, or alternatively, the processing circuitry may determine at least one baseline and/or threshold value based, at least in part, on clinical data (e.g., clinical data sets of patients with known outcomes). In examples in which a threshold value is a patient-specific threshold value, the patient-specific threshold value may be periodically updated, such as to track trends in an absolute value of an intrinsic frequency or in a value of a relationship between a value of a first intrinsic frequency and a value of a second intrinsic frequency over a period of time. In some such examples, a threshold value may be based on one or more values of an absolute value of an intrinsic frequency of the patient or of a relationship between the value of the first intrinsic frequency and the value of the second intrinsic frequency of the patient that correspond to one or more previous monitoring periods. A monitoring period of time may be an hour, day, or any other suitable period of time.

The processing circuitry may update a patient-specific threshold value based on a determination that a predetermined number of monitoring periods has elapsed. For example, if the processing circuitry determines that values of a relationship between the value of the first intrinsic frequency and the value of the second intrinsic frequency are trending upward or downward over one or more previous periods monitoring periods (e.g., over multiple days), the processing circuitry may update a threshold by modifying the threshold value. For example, the processing circuitry may lower an intrinsic frequency difference threshold value that is associated with a higher end of an intrinsic frequency difference range if a value of the difference between the value of the first intrinsic frequency and the value of the second intrinsic frequency is trending upward, thereby increasing the significance of any further increase in the difference between the value of the first intrinsic frequency and the value of the second intrinsic frequency that may occur in subsequent periods of time.

In some examples, the processing circuitry may be configured to apply a cumulative sum technique to values of a patient parameter, such as an intrinsic frequency, a value of a relationship between the first intrinsic frequency and the second intrinsic frequency (e.g., a difference or a ratio), or another patient parameter to determine whether a trend in the patient parameter is indicative of a worsening health condition of the patient. In some such examples, the processing circuitry may adapt a corresponding baseline value of the patient parameter over time based on a relatively longer-term trend in the patient parameter determined over one or more previous monitoring periods and compare a current value of the patient parameter to the corresponding adapted baseline value.

In such examples, the processing circuitry may determine a current index value of the patient parameter based on the comparison of the current value of the patient parameter to the corresponding adapted baseline value. The index value of the patient parameter may be an accumulation of a difference between current values of the patient parameter and the corresponding adapted baseline value over one or more previous monitoring periods. The processing circuitry may adapt the index value by adjusting the index value upward or downward based on a difference between the current value of the patient parameter and the corresponding adapted baseline value. The processing circuitry then may compare the current index value to one or more threshold values associated with a deviation from the trend in the patient parameter that may be indicative of a worsening health condition of the patient (e.g., a large and/or long-term deviation in a direction indicative of the worsening health condition). If the current index value satisfies one or more of the threshold values, the processing circuitry may transmit an alert to a computing device located with the patient or a caregiver and/or to a computing device located with a clinician. If the current index value does not satisfy one or more of the threshold values, the processing circuitry may not transmit an alert and may continue to adjust the index value as appropriate during one or more subsequent monitoring periods. For example, the processing circuitry may continue to adjust the index value upward until the value satisfies one or more threshold values if the deviation from the trend in the patient parameter continues. In this manner, the systems and techniques described herein may enable monitoring of trends in a patient parameter to determine whether a health condition of the patient is worsening or improving. In some examples, the processing circuitry may reset the index value to zero, such as upon detection of a non-physiologic change (e.g., a sufficiently large single-day change in the measured parameter or a measured posture change) or based on a user request to reset the index value to zero, thereby re-starting the cumulative sum technique.

In some examples, a medical device system that includes the processing circuitry may include a medical device configured to deliver cardiac pacing to the patient. In some such examples, the processing circuitry may determine a value of at least one pacing parameter based on the at least one value of the intrinsic frequency of an arterial pressure cycle determined by the processing circuitry. For example, the processing circuitry may determine a value of at least one pacing parameter that may reduce a value of a difference between the value of the first intrinsic frequency and the value of the second intrinsic frequency. A value of the at least one pacing parameter that reduces a value of the difference between the value of the first intrinsic frequency and the value of the second intrinsic frequency may provide improved cardiovascular function, such as by improving energy transfer between portions of the cardiovascular system during the cardiac cycle. After determining the value of the at least one pacing parameter, the processing circuitry may control the medical device to deliver the cardiac pacing at the determined value of the at least one pacing parameter. In some examples, the determined value of the at least one pacing parameter may be a value of at least one cardiac resynchronization therapy (CRT) parameter, and the processing circuitry may control the medical device to deliver the cardiac pacing at the value of the at least one pacing parameter by controlling the medical device to provide CRT. Thus, the techniques described herein may enable the frequent or substantially real-time adaptation of cardiac pacing to meet an individual patient's needs based on at least one value of an intrinsic frequency of an arterial pressure cycle. Example pacing parameters that may be modified by the processing circuitry include an A-V delay, V-V delay, or pacing electrode site/vector.

In some examples, the medical device may be an implantable medical device (IMD) configured for implantation within the patient. The IMD may include a housing, configured for subcutaneous implantation, on which the at least two of the plurality of electrodes is positioned. In some examples, the IMD may be a leadless IMD. In other examples, the medical device may be one or more other implanted or external devices or servers. Examples of the one or more other implanted or external devices may include an implanted, multi-channel cardiac pacemaker, implantable cardioverter-defibrillator (ICD), implantable pulse generator (IPG), leadless (e.g., intracardiac) pacemaker, extravascular pacemaker and/or ICD, an external monitor, a drug pump or other IMD or combination of such IMDs.

In any such examples, the processing circuitry may transmit the heart failure status of the patient to a remote computer, receive instructions from the remote computer for a medical intervention based on the heart failure status of the patient, and transmit the instructions for the medical intervention to a user interface. Such instructions for a medical intervention may include at least one of a change in a drug selection, a change in a drug dosage, instructions to schedule a visit with a clinician, or instructions for the patient to seek medical attention. In this manner, a patient's diagnoses and/or treatment for a heart failure condition may be modified as needed in between clinic visits, which may help avoid adverse medical events such as recurrent symptoms, acute decompensation, or hospitalization. Heart failure, as referred to herein, may include congestive heart failure (CHF), in which the heart failure results in congestion in the body tissues, which may result in edema, such as pulmonary edema.

Although a heart failure status of a patient may be determined based on results of diagnostic or other evaluative procedures (e.g., examination of a cardiac electrogram, blood tests, stress tests, or others), such other techniques for determining heart failure status may require a clinic visit or in-home visit by medical personnel and thus may only be performed infrequently, such as at intervals of one or more weeks or months. Moreover, although some other techniques for determining a heart failure status of a patient may include determining an estimated arterial pressure waveform of the patient, such other techniques also may require a visit with medical personnel. For example, such other techniques may require the use of clinical scanning equipment to obtain an estimated arterial pressure waveform of the patient and/or may require calibration of an arterial pressure signal or combination of the arterial pressure signal with a simultaneously-derived flow signal. Thus, such other techniques may not practicably enable early detection of changes in such physiological functions between clinician visits and before the changes lead to adverse medical events.

Determining or estimating an estimated arterial pressure waveform of the patient based on an arterial impedance signal may help enable determination of the heart failure status of the patient based on information derived from the estimated arterial pressure waveform between clinician visits. For example, animal and human data suggest that bioimpedance (e.g., arterial impedance) measured epidermally or subcutaneously using bipolar, tripolar or quadripolar electrode arrays may provide a signal that is similar in morphometry to an arterial pressure trace. The similarity of the estimated arterial pressure waveform and the arterial impedance signal morphologies may be related to changes in local impedance that are inversely proportional to a diameter of a nearby compliant arterial vessel. Numerous types of medical devices including a plurality of electrodes and configured to be located with a patient outside of the clinical setting may be used to obtain an arterial impedance signal of a patent, such one or more of the implanted or external devices described above. For example, electrodes of some existing medical devices already in use for monitoring physiological parameters of the patient associated with cardiac function and/or delivering cardiac pacing or other therapy may be used for sensing arterial impedance signals. Thus, example techniques described herein may enable use of simpler, multi-function medical devices to detect an estimated arterial pressure waveform of patient 4 instead of relying on sensors other than electrodes to detect the estimated arterial pressure waveform of patient 4.

Processing circuitry of a medical device system including one or more such medical devices may determine an estimated arterial pressure waveform of the patient based on an arterial impedance signal of the patient received from at least two electrodes of the medical device and may use the estimated arterial pressure waveform, as described above, to determine one or more values of an intrinsic frequency at one or more predetermined time intervals throughout the day and/or night. In this manner, arterial impedance signals obtained by one or more medical devices located with the patient between clinic visits may enable determination of the heart failure status of the patient between clinic visits, such as on a daily basis or at any other suitable interval.

In some examples, the techniques described herein may enable identification of changes in a heart failure status of a patient before the changes lead to symptoms, acute decompensation, and/or the progression or the patient's heart failure condition or development of one or more additional medical conditions. Thus, the techniques described herein may help enable determination of possibility that the patient will experience an adverse medical event, which may help clinicians prescribe personalized treatment to help avert hospitalizations, improve clinical outcomes, and/or reduce the economic burden on the health care system.

FIG. 1 illustrates the environment of an example medical device system 2 in conjunction with a patient 4 and a heart 6, in accordance with an apparatus and method of certain examples described herein. The example techniques may be used with an IMD 10, which may be leadless and in wireless communication with external device 12, as illustrated in FIG. 1. In some examples, IMD 10 may take the form of a Reveal LINQ™ Insertable Cardiac Monitor (ICM), available from Medtronic plc, of Dublin, Ireland. In some examples, IMD 10 may be coupled to one or more leads. In some examples, IMD 10 may be implanted outside of a thoracic cavity of patient 4 (e.g., subcutaneously in the pectoral location illustrated in FIG. 1). Electrodes of IMD 10, e.g., formed on the housing of or carried by leads coupled to IMD 10, may be positioned near or within an artery of patient 4. As illustrated in FIG. 1, IMD 10 may be positioned near a left subclavian artery of patient 4, although IMD 10 (e.g., electrodes of IMD 10) may be positioned near any other suitable artery in other examples.

External device 12 may be a computing device configured for use in settings such as a home, clinic, or hospital, and may further be configured to communicate with IMD 10 via wireless telemetry. For example, external device 12 may be coupled to a remote patient monitoring system, such as Carelink®, available from Medtronic plc, of Dublin, Ireland. External device 12 may, in some examples, comprise a programmer, an external monitor, or a consumer device such as a smart phone or tablet. In other examples, the example techniques and systems described herein may be used with an external medical device in addition to, or instead of IMD 10. Such an external medical device may be positioned externally to patient 4 (e.g., positioned on the skin of patient 4) and may carry out any or all of the functions described herein with respect to IMD 10.

Medical device system 2 may include a plurality of electrodes (e.g., for sensing a cardiac function of patient 4). In some examples, the plurality of electrodes may be positioned on a housing of IMD 10. At least two of the plurality of electrodes may detect an arterial impedance signal of patient 4 that enables a processing circuitry of medical device system 2 to determine an estimated arterial pressure waveform of patient 4 based on such signals. Although such processing circuitry may be contained within IMD 10 and/or within another medical device of medical device system 2, e.g., external device 12, the processing circuitry may be described herein as being a component of IMD 10 for the sake of clarity.

The processing circuitry may determine the estimated arterial pressure waveform of the patient based on the arterial impedance signal received from the at least two of the plurality of electrodes. In some examples, a technique by which the processing circuitry estimates the morphometry of the estimated arterial pressure waveform of the patient may include filtering the impedance signal to remove content from the impedance signal. For example, the processing circuitry may filter the impedance signal to remove high frequency content from the signal (e.g., greater than or equal to about 20 hertz (Hz)), very low frequency content (e.g., less than or equal to about 0.05 Hz to about 01. Hz), and/or a DC component of the signal. In some examples, the processing circuitry may determine boundaries of one or more arterial pressure cycles, such as by processing the impedance signal or another signal (e.g., a cardiac electrogram signal) within a window timed from a fiducial associated with a cardiac cycle of patient 4 (e.g., an R-wave and/or any other suitable fiducial). Depending on factors such as the distance of IMD 10 from heart 6, proximity of IMD 10 to an artery of patient 4, and or substantial alignment of IMD 10 with the artery of patient 4, a morphometry of the impedance waveform may be more or less similar to a morphometry of the estimated arterial pressure waveform of patient 4.

For example, the similarity of the morphometries of the impedance waveform and the estimated arterial pressure waveform may increase as a distance between IMD 10 and an artery of patient 4 decreases and/or as the at least two of the plurality of electrodes are positioned in closer alignment with a longitudinal axis of the artery, which may be attributable to a corresponding decrease in the influence of non-arterial tissue impedance on the impedance signal sensed by the at least two of the plurality of electrodes. Additionally, or alternatively, the similarity of the morphometries may increase with increasing distance between heart 6 and IMD 10, which may be attributable to a corresponding decrease in the influence of impedance fluctuations caused by changes in the fluid volume of the left ventricle (LV) of heart 6 on the impedance signal sensed by the at least two of the plurality of electrodes of IMD 10. Thus, in some examples, positioning IMD 10 close to or within an artery of patient 4 and/or relatively further from heart 6 (e.g., within the thoracic region of patient 4) may help enable the electrodes of IMD 10 to detect an arterial impedance signal that fluctuates substantially in correspondence with fluctuations in the estimated arterial pressure waveform of patient 4. In some examples, a housing and/or one or more leads of an IMD of system 2 may provide more than two electrodes, and thus a plurality of associated electrode vectors. In such examples, processing circuitry of system 2 may analyze an arterial impedance signal received from one or more respective electrode vectors of the plurality of electrode vectors and identify an electrode vector of the plurality that provides a suitable arterial impedance signal (e.g., not substantially affected by non-arterial tissue impedance). The processing circuitry, or in some examples a clinician, then may select the identified electrode vector for use in determining the estimated arterial pressure waveform of patient 4.

The estimated arterial pressure waveform may include a plurality of arterial pressure cycles, each of which may correspond to a different cardiac cycle of a plurality of cardiac cycles of patient 4. For at least some of the plurality of cardiac cycles of patient 4, the processing circuitry may determine at least one value of an intrinsic frequency of the corresponding arterial pressure cycle. For example, the processing circuitry may determine least one value of an intrinsic frequency of a corresponding arterial pressure cycle by determining a value of a first intrinsic frequency of a first portion of the corresponding arterial pressure cycle and a value of a second intrinsic frequency of a second portion of the corresponding arterial pressure cycle that is subsequent to the first portion of the corresponding arterial pressure cycle.

In some examples, the processing circuitry may determine the at least one value of an intrinsic frequency of the estimated arterial pressure waveform of patient 4 based on an assumption that an instantaneous frequency of the coupled heart-aorta system and the decoupled aorta are piecewise constant in time, thereby enabling extraction of values of an intrinsic frequency from the estimated arterial pressure waveform. In some examples, an intrinsic frequency may be extracted from the arterial pressure via a waveform norm-2 ($L_2$) minimization method (e.g., a reduction of a sparse time-frequency representation (STFR) method to an $L_2$ minimization problem for periodic signals). In such examples, envelopes of an intrinsic mode function ((IMF); an instantaneous frequency of which may be extracted via application of an adaptive STFR method to a pressure wave) may also be assumed to be piecewise constant in time to distinguish between coupled heart-aorta system and the decoupled aorta. Such an $L_2$ minimization problem for extracting trend and frequency content of an input pressure wave (e.g., an arterial pressure wave) may be defined as follows:

$$\min: \|f(t) - \chi(0, T_0)s_1(t) - \chi(T_0, T)s_2(t) - c\|_2^2, \quad \text{(Expression 1)}$$

Subject to:

$$a1\cos(\omega_1 T_0) | +b1\sin(\omega_1 T_0) = a2\cos(\omega_2 T_0)(\omega_2 T_0), \quad \text{(Equation 1)}$$

$$a_1 = a_2\cos(\omega_1 T) + b_2\sin(\omega_2 T), \quad \text{(Equation 2)}$$

$$s_1(t) = a_1\cos(\omega_1 t) + b_1\sin(\omega_1 t) \text{ and} \quad \text{(Equation 3)}$$

$$s_2(t) = a_2\cos(\omega_2 t) + b_2\sin(\omega_2 t). \text{ Here,} \quad \text{(Equation 4)}$$

$$\chi(a, b) = \begin{cases} 1 & a \leq t \leq b \\ 0 & \text{otherwise} \end{cases}, \quad \text{(Equation 5)}$$

and c is a constant.

The problem reduces to solving for $a_1$, $a_2$, c, $b_1$, $b_2$, $\omega_1$, and $\omega_2$. Equations 1 and 2 are linear constraints ensuring linearity of the trend at time $T_0$, which may be a dicrotic notch of an arterial pressure cycle of patient 4. In examples in which the processing circuitry determines a value of an first intrinsic frequency of a first portion of the corresponding arterial pressure cycle (e.g., prior to the dicrotic notch) and a value of a second intrinsic frequency of a second portion of the corresponding arterial pressure cycle that is subsequent to the first portion of the corresponding arterial pressure cycle (e.g., subsequent to the dicrotic notch), the first intrinsic frequency may be represented by $\omega_1$ and the second intrinsic frequency may be represented by $\omega_2$. The minimization set forth above states that an arterial pressure wave of patient 4 may be approximated by two incomplete sinusoids with different frequencies (e.g., $\omega_1$ and $\omega_2$), which may correspond to respective ones of the value of the first intrinsic frequency and the value of the second intrinsic frequency in one or more of the examples described herein.

The processing circuitry of medical device system 2 may determine the heart failure status of patient 4 based on the value of the first intrinsic frequency and the value of the second intrinsic frequency, such as based on a comparison of the value of the first intrinsic frequency to the value of the second intrinsic frequency. For example, the processing circuitry may determine, for at least some of a plurality of arterial pressure cycles of patient 4 that correspond to at least some of a plurality of cardiac cycles of patient 4, at least one of a difference between the value of the first intrinsic frequency and the value of the second intrinsic frequency or a ratio of the value of the first intrinsic frequency to the value of the second intrinsic frequency and determine the heart failure status of patient 4 based on the at least one of the differences or the ratios.

In some examples, one of the value of the first intrinsic frequency or the value of the second intrinsic frequency may be more predictive of the heart failure condition of the patient than the other. For example, decreasing and/or low (e.g., relative to a baseline) values of a second intrinsic frequency corresponding to a portion of an arterial pressure cycle occurring subsequent to a dicrotic notch of the arterial pressure cycle may be associated physiological phenomena indicative of disease progression, such as increasing arterial stiffness and/or hypertension. In such examples, the processing circuitry may assign a weight to at least one of the value of the first intrinsic frequency or the value of the second intrinsic frequency prior to comparing the value of the first intrinsic frequency to the value of the second intrinsic frequency. The weight assigned by the processing circuitry to a value of an intrinsic frequency of the arterial pressure cycle may be either independent of the value of the intrinsic frequency or may be determined by the processing circuitry at least partially based on the value of the intrinsic frequency. For example, the processing circuitry may assign a different weight to values of an intrinsic frequency within a relatively lower range of values than to values of the intrinsic frequency within a relatively higher range of values. In some examples, a clinician may manually modify weights assigned by the processing circuitry to values of one or more intrinsic frequencies, depending on an individual condition or medical history of patient 4. For example, the clinician may manually modify one or more of the weights assigned by the processing circuitry based on events in the medical history of patient 4 such as hospital admissions for heart failure, medication changes, history of systolic or diastolic heart failure, or hypertension, among others. In any such examples, the weights assigned to the values of the one or more intrinsic frequencies may be stored in a memory of IMD 10 or another device of system 2.

Additionally, or alternatively, the processing circuitry may determine a heart failure status of patient 4 based on a current value of at least one intrinsic frequency. For example, the processing circuitry may determine for at least some of a plurality of arterial pressure cycles of patient 4 that correspond to at least some of a plurality of cardiac cycles of patient 4, at least one current value of an intrinsic frequency of an arterial pressure cycle of patient 4 and compare the at least one current value of the intrinsic frequency to at least one corresponding baseline value of the intrinsic frequency. The current value may be a single value of a current pressure cycle, or a mean, median, or other representative value of frequency values from a plurality of pressure cycles during a current time period, such as a current minute, hour, portion of a day, or day. The baseline value may be a mean, median, or other representative value determined from frequency values of pressure cycles during a past time period. In some such examples, the processing circuitry may determine at least one of a difference between the at least one current value of the intrinsic frequency and the at least one corresponding baseline value of the intrinsic frequency. The processing circuitry then may determine a heart failure status of patient 4 based on the comparison of the at least one current value of the intrinsic frequency and the at least one corresponding baseline value of the intrinsic frequency.

In any such examples, processing circuitry of medical device system 2 may transmit a determined heart failure status of patient 4 to a remote computer (e.g., external device 12). The processing circuitry then may receive instructions for a medical intervention from the remote computer based on the heart failure status of patient 4 and transmit the instructions for the medical intervention to a user interface.

In some examples, an interval at which processing circuitry of medical device system 2 determines a heart failure status of patient 4 is the same as an interval at which the processing circuitry transmits the heart failure status to a remote computer. In other examples, the processing circuitry may determine a heart failure status of patient 4 more frequently than the processing circuitry transmits a heart failure status to the remote computer. By determining a heart failure status more often than a heart failure status is transmitted, an accuracy of a technique for determining a heart failure status may be enhanced by eliminating outlier measurements. For example, the processing circuitry may determine that at least one of the differences between a value of a first intrinsic frequency and a value of a second intrinsic frequency, ratios of the value of the first intrinsic frequency to the value of the second intrinsic frequency, or differences between at least one current value of an intrinsic frequency and at least one corresponding baseline value of the intrinsic frequency satisfies at least one corresponding threshold value only if a certain number or proportion of preceding results satisfied the threshold. In other examples, a single incident in which such a difference or ratio satisfied a threshold may suffice to cause the processing circuitry to determine that a change in the heart failure status of patient 4 has occurred. For the sake of clarity, the differences between a value of a first intrinsic frequency and a value of a second intrinsic frequency, ratios of the value of the first intrinsic frequency to the value of the second intrinsic frequency, or differences between at least one current value of an intrinsic frequency and at least one corresponding baseline value of the intrinsic frequency collectively may be referred to herein as "intrinsic frequency metrics."

In some examples, a clinician may configure a sensitivity of the processing circuitry to different threshold values at or after the time of implant of IMD 10, depending on factors such as the individual condition of patient 4. In examples in which a technique includes comparing a difference between a current value of an intrinsic frequency and a baseline value of the intrinsic frequency to a corresponding threshold value for each of the first intrinsic frequency and the second intrinsic frequency, a clinician may configure the processing circuitry to be more sensitive to values that satisfy a threshold value associated with the second intrinsic frequency. For example, the processing circuitry may determine that the heart failure status of patient 4 has changed if a difference between a current value of the second intrinsic frequency and a baseline value of the second intrinsic frequency satisfies a corresponding threshold value fewer times than may be required for a difference between a current value of the first intrinsic frequency and a baseline value of the first intrinsic frequency, such as depending on which threshold, if satisfied, may be more predictive of an adverse medical event for patient 4. As discussed below, several aspects of the operation of IMD 10 may be configured by a clinician to help achieve improved monitoring and clinical outcomes for individual patients such as patient 4.

In some examples, IMD 10 may be configured to undertake a learning phase after implantation into patient 4. During such a learning phase, the processing circuitry may determine one or more baseline values and one or more threshold values, which the processing circuitry may store in a memory of IMD 10 or other device of medical device system 2. For example, the processing circuitry may determine at least one of a baseline difference between a value of a first intrinsic frequency of an arterial pressure cycle of patient 4 and a value of a second intrinsic frequency of the arterial pressure cycle or a ratio of the value of the first intrinsic frequency to the value of the second intrinsic frequency. Additionally, or alternatively, the processing circuitry may determine at least one baseline value of an intrinsic frequency of an arterial pressure cycle of patient 4, such as a baseline value of a first intrinsic frequency of a first portion of the arterial pressure cycle and/or a baseline value of a second intrinsic frequency of a second portion of the arterial pressure cycle. In some such examples, the processing circuitry may determine a baseline value by averaging or otherwise combining a plurality of difference, ratio, or absolute values of an intrinsic frequency obtained during a plurality of monitoring periods (e.g., a plurality of days). Based on such a determined baseline value, the processing circuitry or a clinician may determine a corresponding threshold value. A threshold value may be a value of an intrinsic frequency metric that is greater than or less than a corresponding baseline value by a predetermined amount indicative of a change in the heart failure status of patient 4.

In any such examples, the processing circuitry may determine the baseline values by determining a mean, median, or other statistical representation of values collected during the training period, although the processing circuitry may use other methods of determining baseline values from collected values. In some examples, the processing circuitry may reject outlier values collected during the training period prior to determining the baseline values based on the remaining collected values. In this manner, a baseline value of an intrinsic frequency metric may be based on a relatively large group of corresponding past values of patient 4. In some examples, the processing circuitry may determine values of an intrinsic frequency of an arterial pressure cycle of patient 4 that are compared to a corresponding baseline value, either directly or by comparison to a threshold value based on a baseline value, based on a relatively smaller group of values. For example, the processing circuitry may determine a value of an intrinsic frequency metric based on a short-term average of a relatively smaller group of recent values of such a difference, ratio, and/or absolute value occurring subsequent to past values of patient 4 on which a corresponding baseline value is based. Thus, in some examples, the processing circuitry may determine a value of one or more intrinsic frequency metrics by averaging or otherwise combining a group of such values.

Because heart failure conditions may be progressive in nature, baseline and/or threshold values associated with patient 4 may be updated periodically. For example, IMD 10 may undertake a new learning phase monthly, quarterly, yearly, or at an expiration of any other appropriate period. The new learning phase may produce new values associated with one or more baseline and/or threshold values described with respect to the techniques described herein, based on an updated heart failure status of patient 4. In other examples, a clinician may program IMD 10 to update such values as needed, such as following a health event experienced by patient 4 that may affect the applicability of such values to one or more aspects of the heart failure status of patient 4.

In addition to or instead of undertaking a new learning phase to determine one or more updated threshold values, the processing circuitry may determine one or more threshold values based on trends in determined values of one or more of a difference, ratio, and/or absolute value of an intrinsic frequency of an arterial pressure cycle of patient 4. Determining one or more threshold values based on such trends may help enable detection of additional aspects of changes in a heart failure state of patient 4. Thus, in some examples, the processing circuitry may determine values an intrinsic frequency metrics and/or one or more corresponding threshold values based on fluctuations in a value of the intrinsic frequency metric of patient 4 that occur across one or more previous predetermined periods of time (e.g., across one or more previous monitoring periods, such as one or more previous days).

In examples in which the processing circuitry determines the heart failure status of patient 4 based on a comparison of at least one of a difference between a value of a first intrinsic frequency and a value of a second intrinsic frequency or a ratio of a value of the first intrinsic frequency to the value of the second intrinsic frequency to at least one corresponding to intrinsic frequency difference threshold or intrinsic frequency ratio threshold, the intrinsic frequency difference threshold value or the intrinsic frequency ratio threshold value may be based on one or more values of such a difference and/or ratio that correspond to one or more previous predetermined periods of time. In examples in which the processing circuitry determines the heart failure status of patient 4 based on a comparison of a difference between current and baseline values of an intrinsic frequency to at least one corresponding intrinsic frequency threshold, the predetermined period of time may be a current predetermined period of time, and at least one corresponding intrinsic frequency threshold value may be based on one or more corresponding previous values of the intrinsic frequency of patient 4 that correspond to one or more previous predetermined periods of time.

Although the example techniques for determining a heart failure status of patient 4 are described herein as being based on the parameter of at least one value of an intrinsic frequency of an arterial pressure cycle, such examples are not intended to be limiting. In some examples, a technique for determining a heart failure status of patient 4 may be based on one or more other physiological parameters that are indicative of the heart failure status of patient 4 in combination with intrinsic frequency of an arterial pressure cycle. Examples of such other parameters, and techniques for determining heart failure status based on a plurality of parameters, are described in U.S. Patent Application Publication No. 2012/0253207 by Sarkar et al. and "Development and validation of an integrated diagnostic algorithm derived from parameters monitored in implantable devices for identifying patients at risk for heart failure hospitalization in an ambulatory setting" by Cowie et al., which are incorporated by reference herein in their entirety.

For example, processing circuitry of medical device system 2 may determine the heart failure status of patient 4 based on a plurality of physiological parameters that include at least one value of an intrinsic frequency and a value of a subcutaneous tissue impedance of the patient. In such examples, the processing circuitry may determine a value of the subcutaneous tissue impedance of patient 4 based on a subcutaneous tissue impedance signal received from at least two of the plurality of electrodes of IMD 10. The at least two of the plurality of electrodes of IMD 10 from which the processing circuitry receives the subcutaneous tissue impedance signal may be the same as or different from the at least two electrodes from which the processing circuitry receives the arterial impedance signal.

The processing circuitry then may determine the heart failure status of patient 4 based on at least one value of an intrinsic frequency metric and the value of the subcutaneous tissue impedance, such as by using a multivariate algorithm, a Bayesian algorithm, or any other suitable method of machine learning. In the example of a Bayesian approach, the model parameters may be determined from clinical data or may be chosen based on empirical assumptions. In some examples, a plurality of physiological parameters may include one or more other physiological parameters, in addition to or instead of subcutaneous tissue impedance, that are indicative of the heart failure status of patient 4, such as augmentation index, reservoir pressure, time to peak pressure, and/or Windkessel parameters (e.g., total arterial compliance, total arterial resistance and characteristic impedance). In some examples, such other physiological parameters may include other physiological parameters more broadly indicative of a health status of patient 4, such as tissue oxygen saturation, pulsatile oxygen saturation, pulse transit time, and/or any other suitable physiological parameter.

In some examples, an example technique for determining a heart failure status of patient 4 based on a plurality of physiological parameters may include one or more aspects of a method for determining heart failure risk status described in U.S. Patent Application Publication No. 2012/0253207 by Sarkar et al. In some such examples, the processing circuitry may determine a heart failure risk level of patient 4, such as a "High," "Medium," or "Low" risk level. The "High" risk level may be associated with a possibility of about 15% or greater that the patient will be hospitalized. The "Low" category may represent diagnostic evaluations in which the possibility of hospitalization for all patient metrics (e.g., metrics based on the plurality of physiological parameters) mostly was at a "Low" level, which may be associated with a possibility of about 5% or less that patient 4 will require hospitalization. The "Medium" category may include other metric state combinations not classified as either "High" or "Low." In some cases, a clinician may evaluate and respond to high and/or medium risk level alerts.

In any such examples, if the one or more previous predetermined periods of time indicate increasingly irregular cardiac function, the processing circuitry may modify a threshold value to provide greater sensitivity to continued fluctuation, such as by raising or lowering a threshold value. In this manner, the processing circuitry may modify the sensitivity of a technique for determining heart failure status by accounting for trends in in determined values of one or more intrinsic frequency metrics of patient 4, which may further help enable detection of changes in a heart failure status of patient 4.

Thus, as described above, the operating parameters of IMD 10 readily may be customized to meet the needs of patient 4, such as by setting baseline and/or threshold values based on the individual attributes of patient 4, such as a heart failure condition or other medical condition of patient and/or an existing medication regimen of patient 4. The extent and ease of customizability of IMD 10 may provide numerous benefits. For example, customizability of IMD 10 to reflect a heart failure condition or existing medication regimen of patient 4 helps ensure that appropriate therapies are prescribed for patient 4, thereby reducing a possibility of human error in prescribing treatment. In addition, in examples in which the processing circuitry (e.g., of IMD 10) one or more baseline and/or threshold values for patient 4, burdens on the time of a clinician and/or other medical personnel may be reduced, which may reduce the time needed for an office visit and promote efficient treatment. Moreover, as discussed above, techniques for using medical device system 2 to determine a heart failure status of patient 4 between visits may help avoid adverse medical events, which may lead to better clinical outcomes such as improved quality of life for patient 4 or reduced medical expenses.

External device 12 may be a computing device (e.g., used in a home, ambulatory, clinic, or hospital setting) to communicate with IMD 10 via wireless telemetry. External device 12 may include or be coupled to a remote patient monitoring system, such as Carelink®, available from Medtronic plc, of Dublin, Ireland. External device 12 may be, as an example, a programmer, external monitor, or a consumer device (e.g., a smart phone). In some examples, external device 12 may receive data, alerts, patient physiological information, or other information from IMD 10.

External device 12 may be used to program commands or operating parameters into IMD 10 for controlling its functioning (e.g., when configured as a programmer for IMD 10). In some examples, external device 12 may be used to interrogate IMD 10 to retrieve data, including device operational data as well as physiological data accumulated in IMD memory. Such interrogation may occur automatically according to a schedule and/or may occur in response to a remote or local user command. Programmers, external monitors, and consumer devices are examples of external devices 12 that may be used to interrogate IMD 10. Examples of communication techniques used by IMD 10 and external device 12 include radiofrequency (RF) telemetry, which may be an RF link established via Bluetooth, Wi-Fi, or medical implant communication service (MICS). In some examples, external device 12 may include a user interface configured to allow patient 4, a clinician, other medical personnel, another caregiver, or any other user to remotely interact with IMD 10.

Medical device system 2 is an example of a medical device system configured to monitor a heart failure status of patient 4 and facilitate updates to patient 4's treatment (e.g., for a heart failure condition) as needed between clinician visits. The techniques described herein may be performed by processing circuitry of a device of medical device system 2, such as processing circuitry of IMD 10. Additionally, or alternatively, the techniques described herein may be performed, in whole or in part, by processing circuitry of external device 12, and/or by processing circuitry of one or more other implanted or external devices or servers (not shown). Examples of the one or more other implanted or external devices may include an implanted, multi-channel cardiac pacemaker, ICD, IPG, leadless (e.g., intracardiac) pacemaker, extravascular pacemaker and/or ICD, or other IMD or combination of such IMDs configured to deliver CRT to heart 6, an external monitor, or a drug pump.

Communication circuitry of each of the devices of medical device system 2 (e.g., IMD 10 and external device 12) may enable the devices to communicate with one another. In addition, although one or more sensors (e.g., electrodes) are described herein as being positioned on a housing of IMD 10, in other examples, such sensors may be positioned on a housing of another device implanted in or external to patient 4. In such examples, one or more of the other devices may include processing circuitry configured to receive signals from the electrodes or other sensors on the respective devices and/or communication circuitry configured to transmit the signals from the electrodes or other sensors to another device (e.g., external device 12) or server.

Figure 2:
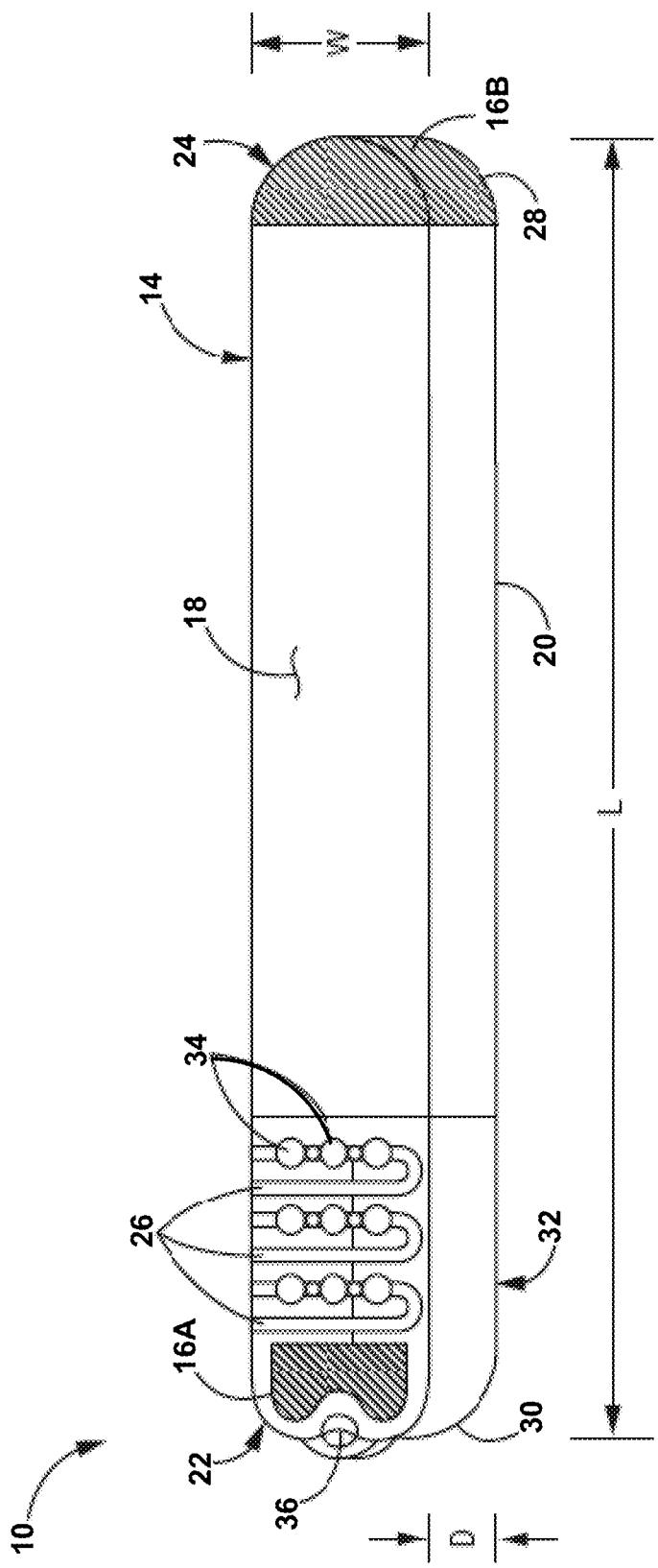
FIG. 2 is a conceptual drawing illustrating an example configuration of the leadless implantable medical device of the medical device system of FIG. 1.
Figure 3:
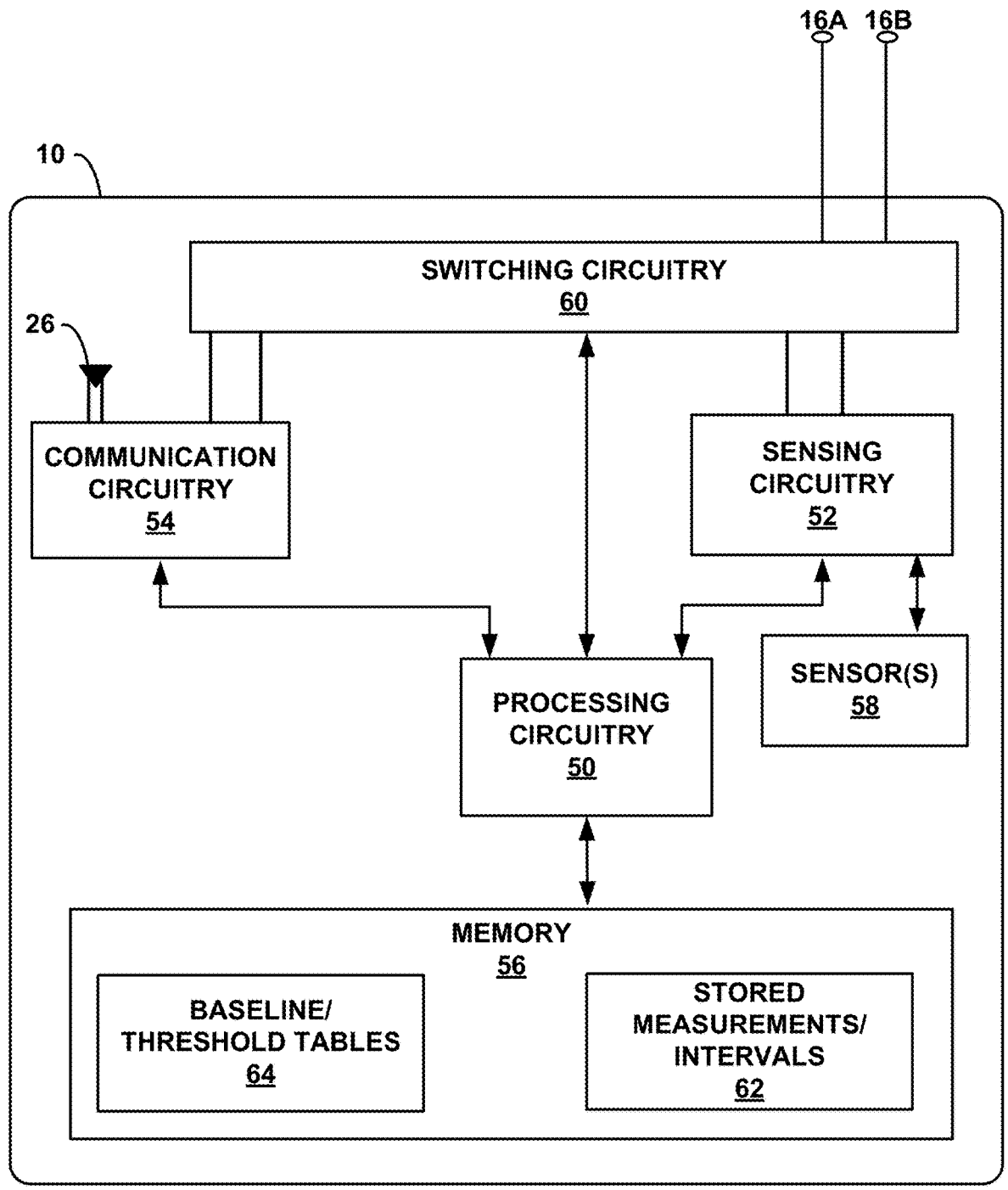
FIG. 3 is a functional block diagram illustrating an example configuration of the leadless implantable medical device of FIG. 1.
Figure 4A:
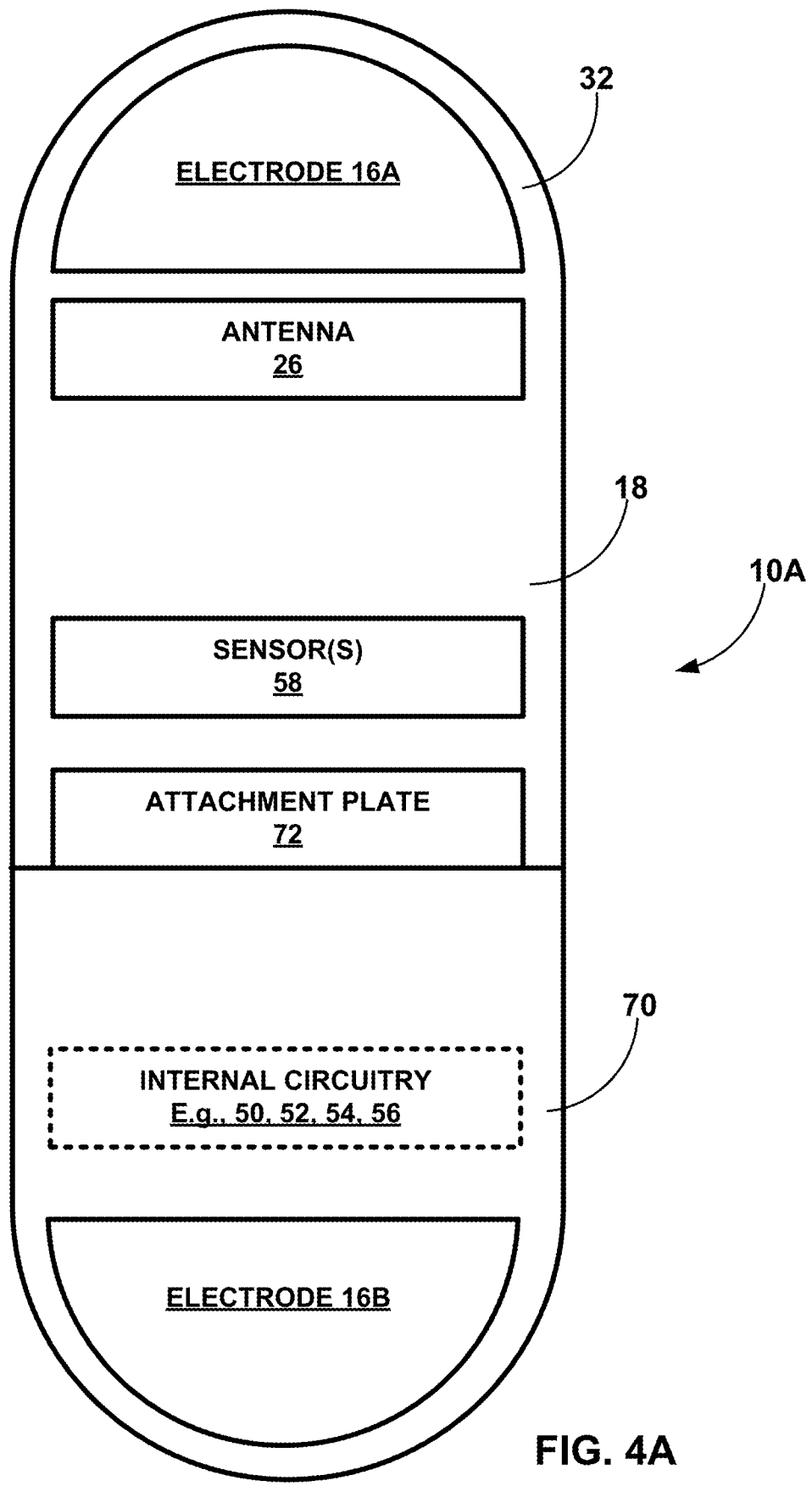

FIGS. 2-4B illustrate various aspects and example arrangements of IMD 10 of FIG. 1. For example, FIG. 2 conceptually illustrates an example physical configuration of IMD 10. FIG. 3 is a block diagram illustrating an example functional configuration of IMD 10. FIGS. 4A and 4B illustrate additional views of an example physical and functional configuration of IMD 10. It should be understood that any of the examples of IMD 10 described below with respect to FIGS. 2-4B may be used to implement the techniques described herein for determining a heart failure status of patient 4.

FIG. 2 is a conceptual drawing illustrating an example configuration of IMD 10 of FIG. 1. In the example shown in FIG. 2, IMD 10 may comprise a leadless, subcutaneously-implantable monitoring device having a housing 14, a proximal electrode 16A, and a distal electrode 16B. Housing 14 encloses electronic circuitry located inside the IMD 10, and protects the circuitry contained therein from fluids such as body fluids. In some examples, 14 may comprise first major surface 18, second major surface 20, proximal end 22, and distal end 24. Proximal electrode 16A and distal electrode 16B may be positioned near respective proximal and distal ends 22 and 24 of IMD 10, such that a spacing between proximal electrode 16A and distal electrode 16B may range from about 30-55 mm, about 35-55 mm, or about 40-55 mm, or more generally from about 25-60 mm. In some examples, IMD 10 may include one or more additional electrodes and/or one or more other sensors (not shown), which may be positioned on one or both of major surfaces 18, 20 of IMD 10. In any such examples, electrical feedthroughs may provide electrical connection of electrodes 16A, 16B or other sensors to circuitry within housing 14.

In the example shown in FIG. 2, IMD 10 is defined by a length L, a width W, and thickness or depth D. In this example, IMD 10 is in the form of an elongated rectangular prism in which length L is significantly greater than width W, and in which width W is greater than depth D. However, other configurations of IMD 10 are contemplated, such as those in which the relative proportions of length L, width W, and depth D vary from those described and shown in FIG. 2. In some examples, the geometry of the IMD 10, such as the width W being greater than the depth D, may be selected to allow IMD 10 to be inserted under the skin of the patient using a minimally invasive procedure and to remain in the desired orientation during insertion. In addition, IMD 10 may include radial asymmetries (e.g., the rectangular shape) along a longitudinal axis of IMD 10, which may help maintain the device in a desired orientation following implantation.

Overall, IMD 10 may have a length L of about 20-30 mm, about 40-60 mm, or about 45-60 mm. In some examples, the width W of first major surface 18 may range from about 3-10 mm, and may be any single width or range of widths between about 3-10 mm. In some examples, a depth D of IMD 10 may range from about 2-9 mm. In other examples, the depth D of IMD 10 may range from about 2-5 mm, and may be any single or range of depths from about 2-9 mm. In any such examples, IMD 10 is sufficiently compact to be implanted within the subcutaneous space of patient 4 in the region of a pectoral muscle.

IMD 10 may have a geometry and size designed for ease of implantation and patient comfort. For example, IMD 10 may have a volume of 3 cubic centimeters ($cm^3$) or less, 1.5 $cm^3$ or less, or any volume therebetween. As illustrated in FIG. 2, proximal end 22 and distal end 24 may be rounded, which may reduce discomfort and/or irritation to surrounding tissue when IMD 10 implanted under the skin of patient 4. An example configuration of IMD 10, including an instrument and method for inserting IMD 10 is described in U.S. Patent Application Publication No. 2014/0276928 by Vanderpool et al., which is incorporated herein by reference in its entirety. An example configuration of IMD 10 also is described in U.S. Pat. No. 9,675,270 by Sarkar, which is incorporated herein by reference in its entirety.

In some examples, IMD 10 may be configured for implantation within patient 4 such that first major surface 18 of IMD 10 faces outward towards the skin when IMD 10 is inserted within patient 4 and second major surface 20 faces inward toward musculature of patient 4. First and second major surfaces 18, 20 may face in directions along a sagittal axis of patient 4, as illustrated in FIG. 1, and this orientation may be maintained upon implantation due to the dimensions of IMD 10. Additionally, or alternatively, IMD 10 may be configured for implantation within patient 4 in one or more other orientations relative to one or more anatomical landmarks of patient 4.

In the example shown in FIG. 2, proximal end 22 of IMD 10 includes header assembly 32 having one or more of integrated antenna 26, anti-migration projections 34, and suture hole 36. Integrated antenna 26 is located on the same major surface (e.g., first major surface 18) as electrode 16A, and may be an integral part of header assembly 32. In other examples, integrated antenna 26 may be formed on the major surface opposite from electrode 16A or may be incorporated within housing 14 of IMD 10. Antenna 26 may be configured to transmit or receive electromagnetic signals for communication. For example, antenna 26 may be configured to transmit to or receive signals from a programmer via inductive coupling, electromagnetic coupling, tissue conductance, Near Field Communication (NFC), Radio Frequency Identification (RFID), Bluetooth®, Wi-Fi, or other proprietary or non-proprietary wireless telemetry communication schemes. Antenna 26 may be coupled to communication circuitry of IMD 10, which may drive antenna 26 to transmit signals to external device 12. Antenna 26 may transmit signals received from external device 12 to processing circuitry of IMD 10 via the communication circuitry.

IMD 10 may include several features for retaining IMD 10 in position once subcutaneously implanted in patient 4. For example, as shown in FIG. 2, housing 14 may include anti-migration projections 34 positioned adjacent integrated antenna 26. Anti-migration projections 34 may comprise a plurality of bumps or protrusions extending away from first major surface 18 and may reduce or prevent movement of IMD 10 after implantation in patient 4. In other examples, anti-migration projections 34 may be located on the opposite major surface as proximal electrode 16A and/or integrated antenna 26. In addition to or instead of anti-migration projections 34, a portion of housing 14 (e.g., header assembly 32) may define a suture hole 36, which may enable a clinician to suture IMD 10 to patient tissue to reduce or prevent movement of IMD 10 after implantation in patient 4. In the example of FIG. 2, suture hole 36 is defined by a portion of header assembly 32 adjacent to proximal electrode 16A. In some examples, header assembly 32 may comprise a molded header assembly made from a polymeric material, which may be integral with or separable from the main portion of IMD 10.

In the example shown in FIG. 2, proximal electrode 16A is in close proximity to proximal end 22, and distal electrode 16B is in close proximity to distal end 24 of IMD 10. In this example, distal electrode 16B is not limited to a flattened, outward facing surface, but may extend from first major surface 18, around rounded edges 28 or end surface 30, and onto the second major surface 20 in a three-dimensional curved configuration. As illustrated, proximal electrode 16A is located on first major surface 18 and is substantially flat and outward facing. However, in other examples not shown here, proximal electrode 16A and distal electrode 16B both may be configured like proximal electrode 16A shown in FIG. 2, or both may be configured like distal electrode 16B shown in FIG. 2. Any of electrodes 16A, 16B may be formed of a biocompatible conductive material. For example, any of electrodes 16A, 16B may be formed from any of stainless steel, titanium, platinum, iridium, or alloys thereof. In addition, electrodes of 1 MB 10 may be coated with a material such as titanium nitride or fractal titanium nitride, although other suitable materials and coatings for such electrodes may be used.

Proximal electrode 16A and distal electrode 16B may be used to sense impedance signals (e.g., arterial impedance signals and/or tissue impedance signals) when 1 MB 10 is implanted subcutaneously in patient 4. In the techniques described herein, processing circuitry of IMD 10 may determine values of at least one intrinsic frequency metric based on the arterial impedance signals. In some examples, electrodes 16A and 16B, or additional electrodes of IMD 10, may be used to sense cardiac electrogram signals when IMD 10 is implanted subcutaneously in patient 4. In such examples, the processing circuitry may determine whether cardiac electrogram signals of patient 4 are indicative of arrhythmia (e.g., the presence or absence of atrial fibrillation and a ventricular rate during atrial fibrillation) or other abnormalities, which the processing circuitry may evaluate in determining whether a cardiac function of patient 4 has changed. Additionally, or alternatively, the processing circuitry may determine a plurality of cardiac cycles of the cardiac electrogram and correlate at least some of the plurality of cardiac cycles to corresponding ones of a plurality of arterial pressure cycles determined based on an estimated arterial pressure waveform of patient 4. The impedance signals and/or cardiac electrogram signals may be stored in a memory of the IMD 10, and data derived from the impedance signals and/or cardiac electrogram signals may be transmitted via integrated antenna 26 to another medical device, such as external device 12.

In some examples, IMD 10 may include one or more additional sensors, such as one or more accelerometers and/or pressure sensors (not shown). Such accelerometers may be 3D accelerometers configured to generate signals indicative of one or more types of movement of the patient, such as gross body movement (e.g., activity) of the patient, patient posture, movements and/or sounds associated with the beating of heart 6, respiration rate, or others. Such pressure sensors may be configured to generate signals indicative of changes in pressure associated with the beating of heart 6, on the basis of which the processing circuitry may determine a heart rate of patient 4. The processing circuitry may use values of physiological parameters determined based on signals from the one or more accelerometers and/or pressure sensors in example techniques for determining the heart failure status of patient 4, such as techniques in which the processing circuitry determines a heart failure status of patient 4 based on one or more other physiological parameters in combination with intrinsic frequency of an arterial pressure cycle.

In some examples, the processing circuitry may determine values of one or more intrinsic frequency metrics at various prescheduled time periods throughout the day and night, which may enable the processing circuitry to distinguish values of intrinsic frequency metrics occurring when patient 4 is substantially inactive (e.g., asleep) from values of intrinsic frequency metrics occurring when patient 4 is active (e.g., awake). Distinguishing values of intrinsic frequency metrics occurring when patient 4 is asleep from such values occurring when patient 4 is awake may help enable medical device system 2 to account for a circadian rhythm of patient 4 when determining the heart failure status of patient 4, as further discussed below with respect to FIG. 3. Thus, in some examples, the processing circuitry may determine whether least one of an activity level, posture, heart rate, or a respiration rate of patient 4, or a time of day, is indicative of patient 4 being substantially inactive (e.g., asleep) or active (e.g., awake) based on the one or more signals received from the one or more accelerometers, pressure sensors, and/or electrodes 16A, 16B.

In some examples, the processing circuitry may determine a value of an intrinsic frequency metric based on at least two values of the intrinsic frequency metric of at least two corresponding arterial pressure cycles of patient 4. For example, in example techniques in which the processing circuitry determines a heart failure status of patient 4 based on a difference between a value of a first intrinsic frequency and a value of a second intrinsic frequency or a ratio of the value of the first intrinsic frequency to the value of the second intrinsic frequency, the processing circuitry may determine one or both of the value of the first intrinsic frequency or the value of the second intrinsic frequency by determining a corresponding representative value of the first intrinsic frequency or the value of the second intrinsic frequency based on a corresponding plurality of the value of the first intrinsic frequency or the value of the second intrinsic frequency. Similarly, in example techniques in which the processing circuitry determines a heart failure status of patient 4 based on a comparison of at least one current value of an intrinsic frequency and at least one corresponding baseline value of the intrinsic frequency, the processing circuitry may determine one or both of the at least one current value and the at least one corresponding baseline value of the intrinsic frequency by determining at least one corresponding representative current value of the intrinsic frequency based on a corresponding plurality of current and/or baseline values of the intrinsic frequency.

In any such examples, the processing circuitry may determine each of a plurality of values of an intrinsic frequency metric by intermittently sampling values of the intrinsic frequency metric during a period of time. For example, the processing circuitry may determine values of the intrinsic frequency metric at 3-minute intervals for a 30 second period each over ten measurement cycles for a total duration of 30 minutes, although any other suitable intervals, number of cycles, or time periods may be used. The processing circuitry then may determine a representative value of the intrinsic frequency metric based on the values of the intrinsic frequency metric collected during the period of time. In some examples, the processing circuitry may reject any outlier values of the intrinsic frequency metric, which may help enhance the accuracy of the determination of the heart failure status of patient 4. The processing circuitry may average the collected measurements, less any rejected outlier values, to determine the representative value, although any other suitable method of data analysis may be used.

Although processing circuitry of IMD 10 is described above as being configured to receive signals from the electrodes 16A, 16B and/or one or more other sensors (e.g., one or more accelerometers or one or more pressure sensors) and determine a value of one or more physiological parameters of patient 4 based on such signals, any steps described herein as being carried out by processing circuitry of IMD 10 may carried out by processing circuitry of one or more devices. For example, processing circuitry of external device 12, or any other suitable implantable or external device or server, may be configured to receive signals from the one or more accelerometers, one or more pressure sensors and/or electrodes 16A, 16B, such as via communication circuitry of IMD 10.

FIG. 3 is a functional block diagram illustrating an example configuration of IMD 10 of FIGS. 1 and 2. As shown in FIG. 3, IMD 10 includes processing circuitry 50 sensing circuitry 52, communication circuitry 54, memory 56, sensors 58, and switching circuitry 60, in addition to previously-described electrodes 16A, 16B, one or more of which may be disposed within housing 14 of IMD 10. In some examples, memory 56 includes computer-readable instructions that, when executed by processing circuitry 50, cause IMD 10 and processing circuitry 50 to perform various functions attributed to IMD 10 and processing circuitry 50 herein. Memory 56 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

In some examples, timing and/or control aspects of processing circuitry 50 may comprise a dedicated hardware circuit, such as an ASIC, separate from other aspects of processing circuitry 50, such as a microprocessor, or a software module executed by a component of processing circuitry 50 (e.g., a microprocessor or ASIC). In some examples, timing and/or control aspects of processing circuitry 50 may be configured to associate current values of an intrinsic frequency of an arterial pressure cycle with a particular time of day, such as day time or night time, so as to enable processing circuitry 50 to take into account a circadian rhythm of patient 4 when determining the heart failure status of patient 4. For example, arterial pressure values and/or heart rate values of patient 4 generally may decrease when patient 4 is asleep (e.g., nighttime), and increase when patient 4 is awake (e.g., daytime).

In some such examples, IMD 10 may be configured to use different (e.g., lower) baseline value and/or threshold values for an intrinsic frequency metric, at times when patient 4 is likely to be asleep than when patient 4 is likely to be awake. For example, processing circuitry may treat daytime and nighttime values of an intrinsic frequency metric as separate, independent parameters, with separate associated baseline and/or threshold values. In some examples in which IMD 10 includes one or more accelerometers, processing circuitry 50 may cross-reference a time of day indicated by timing and/or control aspects of processing circuitry 50 with accelerometer data, such as to confirm whether patient 4 is asleep or awake as predicted based on the time of day. In this manner, timing and/or control aspects of processing circuitry 50 may enhance the ability of IMD 10 to accurately determine a heart failure status of patient 4.

Memory 56 may store determined values of one or more intrinsic frequency metrics of patient 4 and/or one or more intervals or time periods according to which processing circuitry 50 may determine values of one or more intrinsic frequency metrics in stored measurements/intervals 62. Memory 56 also may store baseline and/or threshold values, which processing circuitry 50 may determine during a learning phase of IMD 10, in tables 64. In some examples, processing circuitry may determine an intrinsic frequency difference or ratio threshold value based on a determined baseline difference between a baseline value of a first intrinsic frequency of an arterial pressure cycle of patient 4 and a baseline value of a second intrinsic frequency of the arterial pressure cycle.

For example, processing circuitry 50 may receive at least one baseline arterial impedance signal from electrodes of IMD 10 (e.g., electrodes 16A, 16B). Processing circuitry 50 then may determine a baseline arterial pressure waveform based on the arterial impedance signal and determine a patient-specific baseline value of a first intrinsic frequency of a first portion of an arterial pressure cycle of patient 4 and a patient-specific baseline value of a second intrinsic frequency of a second portion of the arterial pressure cycle subsequent to the first portion based on the baseline arterial pressure waveform. Processing circuitry 50 then may determine at least one of a baseline difference between a value of a first intrinsic frequency and a value of a second intrinsic frequency or a baseline ratio of the value of the first intrinsic frequency to the value of the second intrinsic frequency based on the baseline value of the first intrinsic frequency and the baseline value of the second intrinsic frequency.

Processing circuitry 50 similarly may determine one or more of baseline and/or threshold values in examples in which processing circuitry 50 determines the heart failure status of patient 4 based on a difference between a current value of an intrinsic frequency and a baseline value of the intrinsic frequency. For example, processing circuitry 50 may determine a patient-specific baseline value of the intrinsic frequency by receiving a baseline arterial impedance signal from sensors 58 (e.g., from at least two electrodes of IMD 10), determining a baseline arterial pressure waveform based on the arterial impedance signal, and determining the patient-specific value of the baseline intrinsic frequency based on the baseline arterial pressure waveform. In any such examples, tables 64 may include pre-programmed baseline and/or threshold values that a clinician may select for patient 4 during setup of IMD 10 or manually enter based on the clinician's assessments of patient 4.

Sensing circuitry 52 and communication circuitry 54 may be selectively coupled to electrodes 16A, 16B via switching circuitry 60 as controlled by processing circuitry 50. Sensing circuitry 52 may monitor signals from electrodes 16A, 16B in order to monitor arterial impedance of patient 4 from which processing circuitry 50 may determine an estimated arterial pressure waveform of patient 4 and/or values of one or more intrinsic frequency metrics of patient 4. In some examples in which IMD 10 includes one or more accelerometers and/or pressure sensors, sensing circuitry 52 also may monitor signals from sensors 58, which may include such accelerometers and/or pressure sensors. In some examples, sensing circuitry 52 may include one or more filters and amplifiers for filtering and amplifying signals received from one or more of electrodes 16A, 16B and/or other sensors 58, such as by filtering the arterial impedance signal received from electrodes 16A, 16B to enable processing circuitry 50 to identify one or more components of the arterial impedance signal that vary with arterial pressure, such that intrinsic frequency metrics of the estimated arterial pressure waveform may be derived from those components.

In some examples, sensing circuitry 52 and/or processing circuitry 50 may include a rectifier, filter and/or amplifier, a sense amplifier, comparator, and/or analog-to-digital converter. Upon receiving signals from electrodes 16A, 16B and/or other sensors 58 via sensing circuitry 52, processing circuitry 50 may determine, for at least some of a plurality of cardiac cycles of patient 4, at least one value of an intrinsic frequency of a corresponding arterial pressure cycle of a plurality of arterial pressure cycles of the estimated arterial pressure waveform of patient 4. Processing circuitry 50 then may determine a heart failure status of patient 4 based on the at least one value of the intrinsic frequency, such as based on differences between a value of a first intrinsic frequency and a value of a second intrinsic frequency, ratios of the value of the first intrinsic frequency to the value of the second intrinsic frequency, or differences between at least one current value of an intrinsic frequency and at least one corresponding baseline value. For example, processing circuitry 50 may determine the heart failure status of patient 4 based on whether such a difference or ratio satisfies a corresponding intrinsic frequency difference threshold value, intrinsic frequency ratio threshold value, or intrinsic frequency threshold value stored in tables 64.

Communication circuitry 54 may include any suitable hardware, firmware, software or any combination thereof for communicating with another device, such as external device 12 or another medical device or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. In some examples, communication circuitry 54 may communicate with external device 12. In addition, processing circuitry 50 may communicate with a networked computing device via an external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device. In some examples, the clinician may select one or more baseline and/or threshold values associated with one or more intrinsic frequency metrics, times of day during which patient 4 is expected to be awake or asleep, predetermined periods of time, a number of measurements to be completed during a period, or other parameters of IMD 10.

One or more components of IMD 10 may be coupled a power source, which may include a rechargeable or non-rechargeable battery positioned within housing 14 of IMD 10. A non-rechargeable battery may be selected to last for several years, while a rechargeable battery may be inductively charged from an external device, e.g., on a daily or weekly basis.

FIGS. 4A and 4B illustrate two additional example IMDs that may be substantially similar to IMD 10 of FIGS. 1-3, but which may include one or more additional features. The components of FIGS. 4A and 4B may not necessarily be drawn to scale, but instead may be enlarged to show detail. FIG. 4A is a block diagram of a top view of an example configuration of an IMD 10A. FIG. 4B is a block diagram of a side view of example IMD 10B, which may include an insulative layer as described below.

FIG. 4A is a conceptual drawing illustrating another example IMD 10A that may be substantially similar to IMD 10 of FIG. 1. In addition to the components illustrated in FIGS. 1-3, the example of IMD 10 illustrated in FIG. 4A also may include a body portion 70 and an attachment plate 72. Attachment plate 72 may be configured to mechanically couple header 32 to body portion 70 of IMD 10A. Body portion 70 of IMD 10A may be configured to house one or more of the internal components of IMD 10 illustrated in FIG. 3, such as one or more of processing circuitry 50, sensing circuitry 52, communication circuitry 54, memory 56, and/or internal components of sensors 58. In some examples, body portion 70 may be formed of one or more of titanium, ceramic, or any other suitable biocompatible materials.

FIG. 4B is a conceptual drawing illustrating another example IMD 10B that may include components substantially similar to IMD 10 of FIG. 1. In addition to the components illustrated in FIGS. 1-3, the example of IMD 10B illustrated in FIG. 4B also may include a wafer-scale insulative cover 74, which may help insulate electrical signals passing between electrodes 16A, 16B on housing 14B and processing circuitry 50. In some examples, insulative cover 74 may be positioned over an open housing 14 to form the housing for the components of IMD 10B. One or more components of IMD 10B (e.g., antenna 26, processing circuitry 50, sensing circuitry 52, and/or communication circuitry 54 may be formed on a bottom side of insulative cover 74, such as by using flip-chip technology. Insulative cover 74 may be flipped onto a housing 14B. When flipped and placed onto housing 14B, the components of IMD 10B formed on the bottom side of insulative cover 74 may be positioned in a gap 78 defined by housing 14B. Housing 14B may be formed from titanium or any other suitable material (e.g., a biocompatible material), and may have a thickness of about 200 micrometers to about 500 micrometers. These materials and dimensions are examples only, and other materials and other thicknesses are possible for devices of this disclosure.

Figure 5:
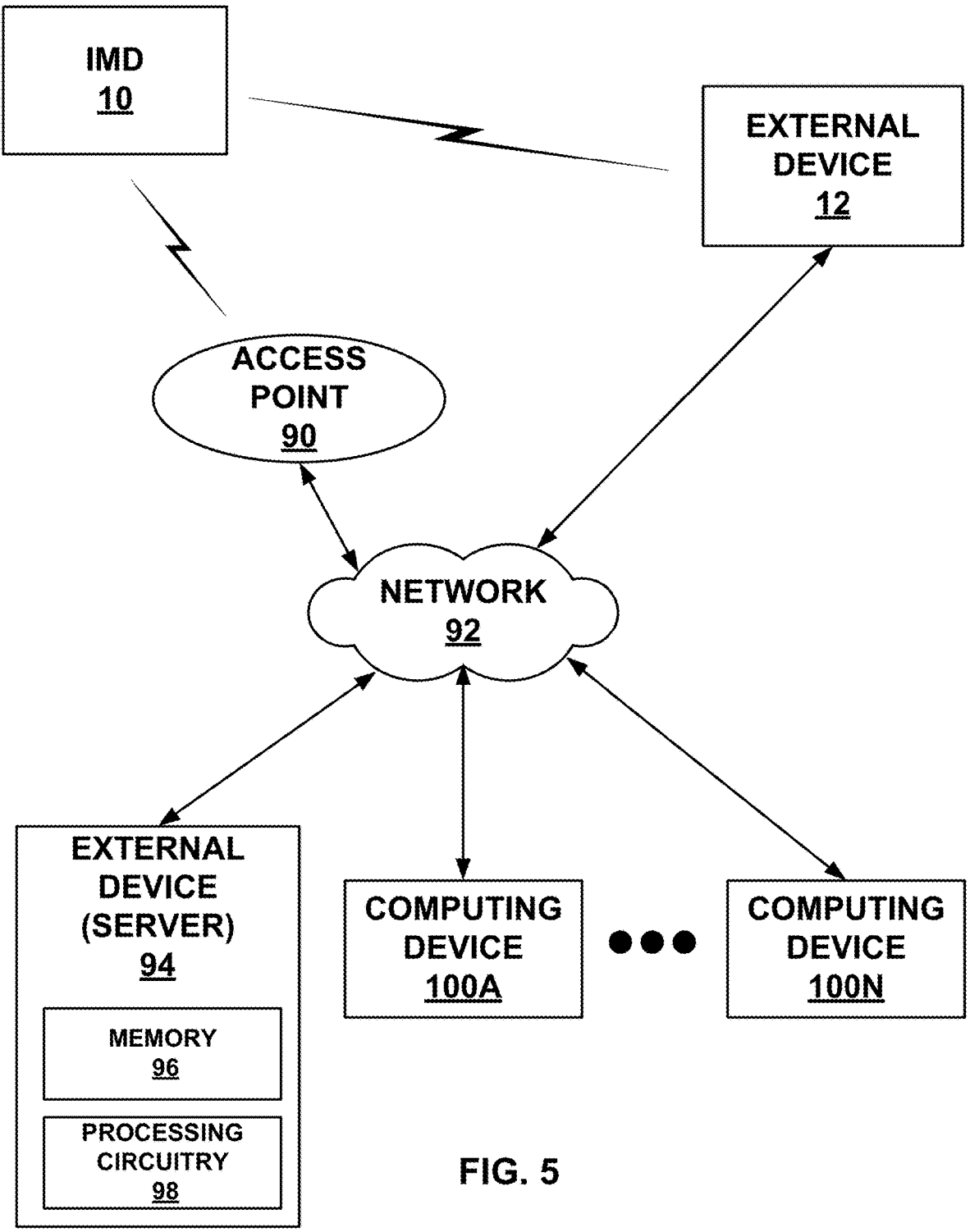
FIG. 5 is a block diagram illustrating an example system that includes an external device, such as a server, and one or more computing devices that are coupled to the leadless implantable medical device of FIG. 1 and the external device of FIG. 1 via a network.

FIG. 5 is a functional block diagram illustrating an example system that includes an access point 90, a network 92, external computing devices, such as a server 94, and one or more other computing devices 100A-100N, which may be coupled to IMD 10, external device 12, and external device 12 via network 92. In this example, IMD 10 may use communication circuitry 54 to communicate with external device 12 via a first wireless connection, and to communicate with an access point 90 via a second wireless connection. In the example of FIG. 5, access point 90, external device 12, server 94, and computing devices 100A-100N are interconnected and may communicate with each other through network 92.

Access point 90 may comprise a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. As discussed above, IMD 10 may be configured to transmit data, such as current values and heart failure statuses, to external device 12. In addition, access point 90 may interrogate IMD 10, such as periodically or in response to a command from the patient or network 92, in order to retrieve current values or heart failure statuses determined by processing circuitry 50 of IMD 10, or other operational or patient data from IMD 10. Access point 90 may then communicate the retrieved data to server 94 via network 92.

In some cases, server 94 may be configured to provide a secure storage site for data that has been collected from IMD 10, and/or external device 12. In some cases, server 94 may assemble data in web pages or other documents for viewing by trained professionals, such as clinicians, via computing devices 100A-100N. One or more aspects of the illustrated system of FIG. 5 may be implemented with general network technology and functionality, which may be similar to that provided by the Medtronic CareLink® Network developed by Medtronic plc, of Dublin, Ireland.

In some examples, one or more of computing devices 100A-100N (e.g., device 100A) may be a tablet or other smart device located with a clinician or other medical personnel or caregiver, by which such a user may program, receive alerts from, and/or interrogate IMD 10. For example, the user may access determined values of one or more intrinsic frequency metrics of patient 4 and/or other information associated with the heart failure status of patient 4 through device 100A, such as when patient 4 is in in between clinic or in-home visits, to check on a heart failure status of patient 4 as desired. In some examples, the user may enter instructions for a medical intervention for patient 4 into an app in device 100A, such as based on a heart failure status of patient 4 determined by IMD 10 and/or other patient data known to the user. Device 100A then may transmit the instructions for medical intervention to another of computing devices 100A-100N (e.g., device 100B) located with patient 4 or another caregiver of patient 4. For example, such instructions for medical intervention may include an instruction to change a drug dosage, timing, or selection, to schedule a visit with the user, or to seek medical attention. In further examples, device 100B may generate an alert to patient 4 based on a health status of patient 4 determined by IMD 10, which may enable patient 4 proactively to seek medical attention prior to receiving instructions for a medical intervention. In some examples, the alert generated by device 100B may include an updated diagnosis of one or more health conditions such as a heart failure condition. For example, the alert may include a diagnosis that a heart failure condition of patient 4 has progressed from a first type of heart failure condition to a second type of heart failure condition. In this manner, patient 4 may be empowered to take action, as needed, to address his or her heart failure status, which may help improve clinical outcomes for patient 4.

FIGS. 6-9 are flow diagrams illustrating various techniques related to determining a heart failure status of a patient based on at least one value of an intrinsic frequency metric of an arterial pressure cycle corresponding to a cardiac cycle of the patient and transmitting instructions for medical intervention to a user interface. As described herein, the techniques illustrated FIGS. 6-9 may be employed using one or more components of medical device system 2, which have been described above with respect to FIGS. 1-5. Although described as being performed by processing circuitry 50 of IMD 10 for the sake of clarity, the techniques of FIGS. 6-9 may be performed, in whole or in part, by processing circuitry and memory of other devices of medical device system 2, as described herein. For example, one or more devices (e.g., external device 12 or other external device or server) or a user such as a clinician or other medical personnel may, in some examples, carry out one or more steps attributed below to processing circuitry 50 of IMD 10.

Figure 6:
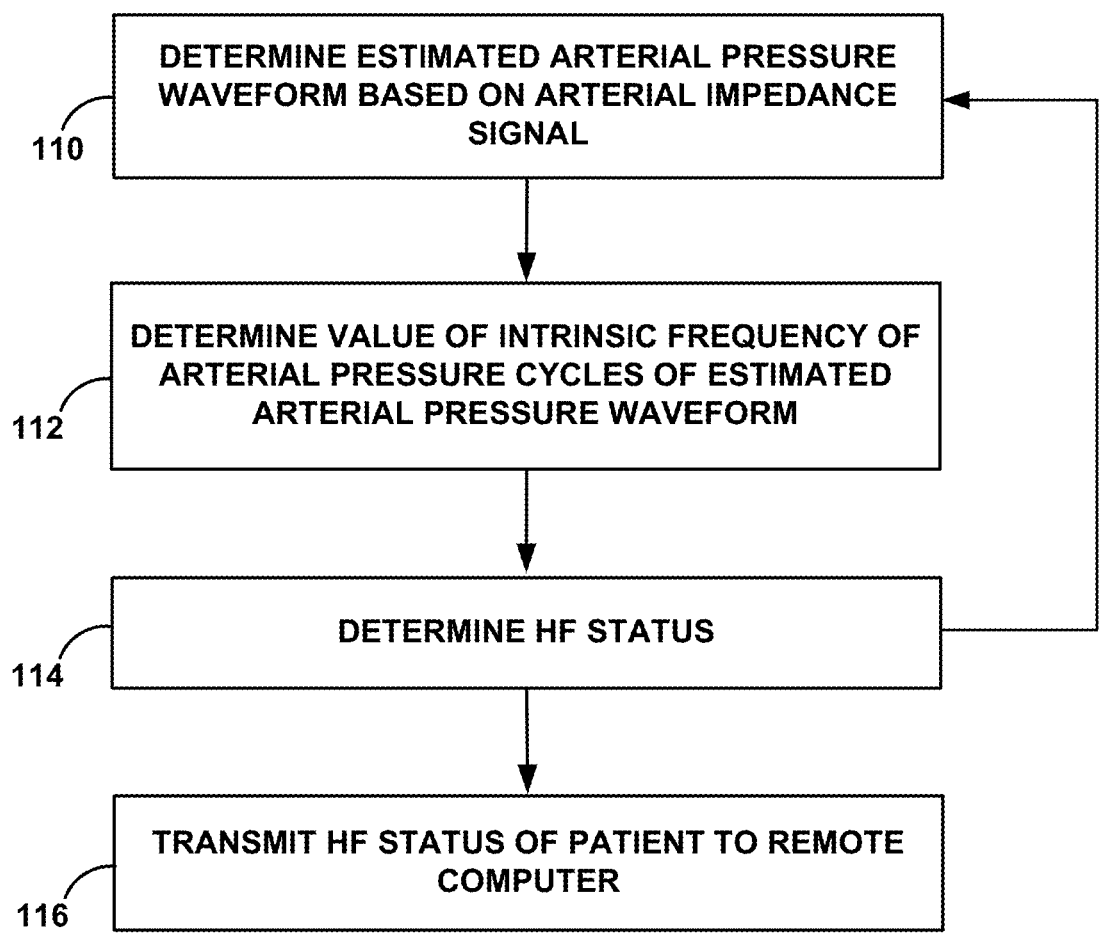
FIG. 6 is a flow diagram illustrating an example technique for determining a heart failure status of a patient based on at least one value of an intrinsic frequency of at least some of a plurality of arterial pressure cycles corresponding to at least some of a plurality of cardiac cycles of the patient and transmitting the heart failure status to a remote computer.

FIG. 6 is a flow diagram illustrating an example technique for determining, by processing circuitry of medical device system 2 (e.g., processing circuitry 50 of IMD 10), a heart failure status of patient 4 based on at least one value of an intrinsic frequency of at least some of a plurality of arterial pressure cycles corresponding to at least some of a plurality of cardiac cycles of patient 4. An intrinsic frequency of an arterial pressure cycle may be, for example, a value of a dominant frequency of a portion of an arterial pressure cycle around which an instantaneous frequency of a portion of the corresponding arterial pressure cycle oscillates (e.g., during a cardiac cycle). According to the example of FIG. 6, processing circuitry 50 determines an estimated arterial pressure waveform of patient 4 based on an arterial impedance signal received from at least two of the plurality of electrodes of IMD 10 (e.g., electrodes 16A, 16B) (110). The estimated arterial pressure waveform of patient 4 includes a plurality of arterial pressure cycles and each of the plurality of arterial pressure cycles corresponds to a different cardiac cycle of a plurality of cardiac cycles of patient 4.

After determining the estimated arterial pressure waveform of patient 4, processing circuitry 50 then determines, for at least some of the plurality of cardiac cycles of patient 4, at least one value of an intrinsic frequency of the corresponding arterial pressure cycle (112). In some examples, processing 50 may determine the at least one value of the intrinsic frequency by determining a representative value of the intrinsic frequency based on at least two values of the intrinsic frequency of at least two corresponding arterial pressure cycles. Processing circuitry 50 then determines the heart failure status of patient 4 based on the at least one value of the intrinsic frequency (114). For example, processing circuitry 50 may compare the at least one value of the intrinsic frequency to at least one intrinsic frequency threshold value and determine the heart failure status of the patient based on the comparison. In some such examples, the plurality of arterial pressure cycles of the estimated arterial pressure waveform of patient 4 may include at least one current arterial pressure cycle and at least one previous arterial pressure cycle.

In some examples, processing circuitry 50 may periodically determine an updated value of the intrinsic frequency threshold based on the at least one value of the intrinsic frequency of the at least one previous arterial pressure cycle, which may enable processing circuitry 50 to track trends in the value of the intrinsic frequency over multiple predetermined periods of time (e.g., days). For example, if processing circuitry 50 determines that values of the intrinsic frequency are trending upward or downward over one or more past predetermined periods of time, processing circuitry 50 may update the intrinsic frequency threshold by modifying the intrinsic frequency threshold value. For example, processing circuitry 50 may raise an intrinsic frequency threshold value if values of the intrinsic frequency trending downward, thereby increasing the significance of any further decrease in the value of the intrinsic frequency that may occur in subsequent predetermined periods of time.

In some examples, processing circuitry 50 may be configured to apply a cumulative sum technique to determine whether a value of a patient parameter, such as an intrinsic frequency, a value of a relationship between the first intrinsic frequency and the second intrinsic frequency (e.g., a difference or a ratio), or a value of another patient parameter to determine whether a trend in the patient parameter is indicative of a worsening health condition of patient. In some such examples, processing circuitry 50 may adapt a corresponding baseline value of the patient parameter over time based on a long-term trend in the patient parameter determined over one or more previous monitoring periods and compare a current value of the patient parameter to the corresponding adapted baseline value. An example of a cumulative sum technique that monitors trends in a patent parameter over time is described in U.S. Pat. No. 7,986,994 to Stadler et al., which is entitled, "METHOD AND APPARATUS FOR DETECTING CHANGE IN INTRATHORACIC ELECTRICAL IMPEDANCE," and issued on Jul. 26, 2011. U.S. Pat. No. 7,986,994 to Stadler et al. is incorporated herein by reference in its entirety.

Processing circuitry 50 then may determine a current index value of the patient parameter based on the comparison of the current value of the patient parameter to the corresponding adapted baseline value. The index value of the patient parameter may be an accumulation of a difference between current values of the patient parameter and the corresponding adapted baseline value over one or more previous monitoring periods. For example, processing circuitry 50 may adjust the index value upward or downward based on a difference between the current value of the patient parameter and the corresponding adapted baseline value. Processing circuitry 50 then may compare the current index value to one or more threshold values associated with a deviation from the trend in the patient parameter that may be indicative of a worsening health condition of patient 4 (e.g., a large and/or long-term deviation in a direction indicative of the worsening health condition). If the current index value satisfies one or more of the threshold values, processing circuitry 50 may transmit an alert to a device located with patient 4 or a caregiver (e.g., external device 12) and/or to a computing device located with a clinician. If the current index value does not satisfy one or more of the threshold values, processing circuitry 50 may not transmit an alert and may continue to adjust the index value as appropriate during one or more subsequent monitoring periods. For example, processing circuitry 50 may continue to adjust the index value upward until the value satisfies one or more threshold values if the deviation from the trend. In this manner, medical device system 2 may enable monitoring of trends in a patient parameter to determine whether a health condition of patient 4 is worsening or improving.

Processing circuitry 50 may repeat blocks 110-114 to periodically determine updated heart failure statuses of patient 4 such as daily, weekly, monthly, yearly, or at any other suitable period. In some examples, the heart failure status of patient 4 may indicate a possibility that patient 4 may experience an adverse medical event within a certain period of time, such as a recurrence of symptoms, acute heart failure decompensation, or other adverse medical events that may require medical intervention such as hospitalization. In some examples, an intrinsic frequency threshold value or intrinsic frequency difference threshold value associated with a change in the heart failure status of patient 4 may be associated with the interval at which processing circuitry 50 periodically determines the updated heart failure status of patient 4. For example, a threshold value associated with a relatively shorter (e.g., daily or weekly) period of time may be higher than a threshold value associated with a relatively longer (e.g., monthly or yearly) period of time. In some such examples, gradual changes that occur in a value of an intrinsic frequency difference or ratio of patient 4 that occur over a longer period of time may be indicative of a change in the heart failure status of patient 4, whereas the same change occurring over a shorter period of time may not necessarily be indicative of a change in the heart failure status of patient 4. For example, such gradual changes may be indicative of long-term worsening or improvement of a heart failure condition of patient 4. In this manner, the techniques described herein may be adapted to periodically determining a heart failure status of patient 4 at one or more suitable intervals.

Processing circuitry then transmits the health status of patient 4 to a remote computer, such as external device 12 (116). In some examples, processing circuitry 50 may transmit the heart failure status of patient 4 to the remote computer each time processing circuitry 50 determines the heart failure status of patient 4. In other examples, processing circuitry 50 may transmit the heart failure status of patient 4 to the remote computer less frequently, such as weekly or at any other suitable interval.

Figure 7:
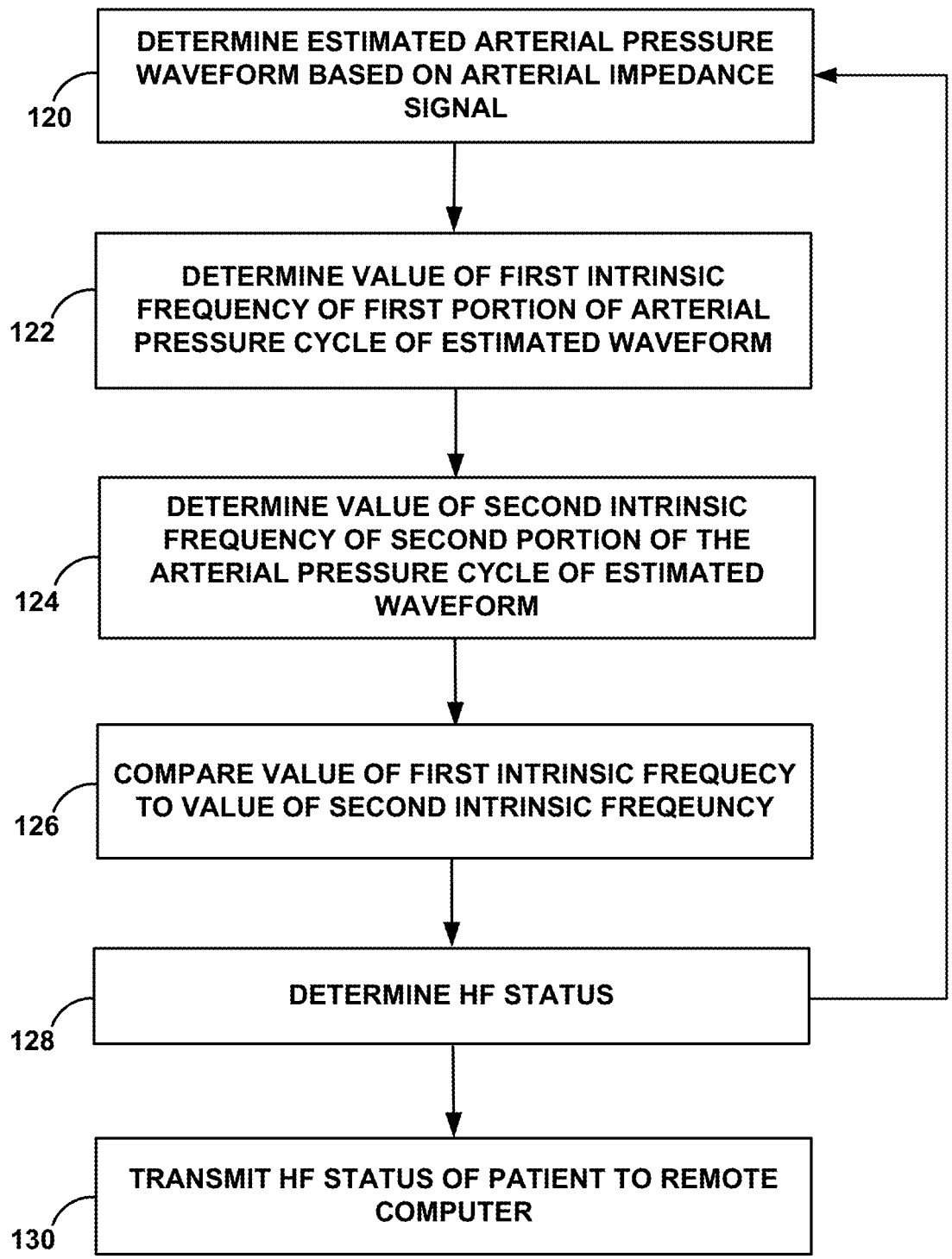
FIG. 7 is a flow diagram illustrating an example technique for determining a heart failure status of a patient based on a comparison of a value of a first intrinsic frequency of a first portion of an arterial pressure cycle to a value of a second intrinsic frequency of a second portion of the arterial pressure cycle and transmitting the heart failure status to a remote computer.

FIG. 7 is a flow diagram illustrating an example technique for determining, by processing circuitry of medical device system 2 (e.g., processing circuitry 50 of IMD 10), a heart failure status of patient 4 based on a comparison of a first value of on a comparison of a value of a first intrinsic frequency of an arterial pressure cycle of patient 4 to a value of a second intrinsic frequency of a second portion of the arterial pressure cycle of patient 4. In some examples, FIG. 7 may be an example of technique of FIG. 6. Thus, one or more aspects of the example technique illustrated in FIG. 7 may be substantially similar to one or more aspects of the example techniques illustrated in FIG. 6. According to the example of FIG. 7, processing circuitry 50 determines an estimated arterial pressure waveform of patient 4 based on an arterial impedance signal received from at least two of the plurality of electrodes of IMD 10 (e.g., electrodes 16A, 16B) (120), substantially as discussed above with respect to FIG. 6. The estimated arterial pressure waveform of patient 4 includes a plurality of arterial pressure cycles and each of the plurality of arterial pressure cycles corresponds to a different cardiac cycle of a plurality of cardiac cycles of patient 4.

For example, processing circuitry 50 may determine least one value of an intrinsic frequency of a corresponding arterial pressure cycle by determining a value of a first intrinsic frequency of a first portion of the corresponding arterial pressure cycle (122) and determining a value of a second intrinsic frequency of a second portion of the corresponding arterial pressure cycle that is subsequent to the first portion of the corresponding arterial pressure cycle (124). In some examples, the first portion of the corresponding arterial pressure cycle occurs prior to a dicrotic notch of the corresponding arterial pressure cycle and the second portion of the corresponding arterial pressure cycle occurs subsequent to the dicrotic notch of the corresponding arterial pressure cycle. As discussed above, an increase in the value of the difference between the value of the first intrinsic frequency and the value of the second intrinsic frequency, or a decrease in the value of the ratio of the value of the first intrinsic frequency to the value of the second intrinsic frequency, may be indicative of worsening heart failure of patient 4.

After determining the value of a first intrinsic frequency of the corresponding arterial pressure cycle and the value of the second intrinsic frequency of the corresponding arterial pressure cycle, processing circuitry 50 then compares the value of a first intrinsic frequency to the value of the second intrinsic frequency (126). For example, processing circuitry 50 may compare the value of the first intrinsic frequency to the value of the second intrinsic frequency by determining at least one of a difference between the value of the first intrinsic frequency and the value of the second intrinsic frequency or a ratio of the value of the first intrinsic frequency to the value of the second intrinsic frequency, although any other suitable relationship between the value of the first frequency and the value of the second frequency may be used.

After comparing the value of the first intrinsic frequency to the value of the second intrinsic frequency, such as by determining the at least one of the difference between the value of the first intrinsic frequency and the value of the second intrinsic frequency or the ratio of the value of the first intrinsic frequency to the value of the second intrinsic frequency, processing circuitry 50 determines a heart failure status of patient 4 based on the comparison (128). Processing circuitry 50 may determine the heart failure status of patient 4 by determining whether the value of such a difference or ratio satisfies at least one corresponding intrinsic frequency difference threshold value or at least one corresponding intrinsic frequency difference threshold value associated with a change in the heart failure status of patient 4, which may be stored in baseline/threshold tables 64 of memory 56.

In some examples, processing circuitry 50 may periodically determine an updated value of an intrinsic frequency difference threshold and/or an updated value of an intrinsic frequency ratio threshold, which may enable processing circuitry 50 to track trends in the relationship between the value of the first intrinsic frequency and the value of the second intrinsic frequency over multiple predetermined periods of time. The at least one of the difference between the value of the first intrinsic frequency and the value of the second intrinsic frequency or the ratio of the value of the first intrinsic frequency to the value of the second intrinsic frequency may correspond to a current predetermined period of time. In some such examples, processing circuitry 50 may determine the intrinsic frequency difference threshold value and/or the intrinsic frequency ratio threshold value based on one or more values of at least one such difference or ratio that correspond to one or more previous predetermined periods of time.

In some examples, an intrinsic frequency difference threshold value or an intrinsic frequency ratio threshold value may be an absolute value of a percentage of at least one baseline value of the corresponding at least one of the difference between the value of the first intrinsic frequency and the value of the second intrinsic frequency or the ratio of the value of the first intrinsic frequency to the value of the second intrinsic frequency, which may be at least one baseline value specific to patient 4. For example, if a baseline value of the difference between the value of the first intrinsic frequency and the value of the second intrinsic frequency=X, then an intrinsic frequency difference threshold value may be X±0.2X. In other examples, the difference between the value of the first intrinsic frequency and the value of the second intrinsic frequency may be associated with multiple intrinsic frequency difference threshold values that correspond to different percentages of the baseline value, thereby taking into account differences in significance between values that exceed a baseline value and values that are less than a baseline value. For example, if a baseline value of the difference between the value of the first intrinsic frequency and the value of the second intrinsic frequency=X, then intrinsic frequency difference threshold values of the difference between the value of the first intrinsic frequency and the value of the second intrinsic frequency may be X+0.2X and X−0.1X. In such an example, values of the difference between the value of the first intrinsic frequency and the value of the second intrinsic frequency that are greater than X, which may be associated with an advanced stage of a heart failure condition of patient 4, may have relatively greater significance than values of that are greater than X, although the relative significance of difference values may be determined based on the individual patient. In any such examples, the threshold values may be based on deviations from corresponding baseline values, such as standard deviations or any other suitable statistical functions.

As with blocks 110-114 of the example of FIG. 6, processing circuitry 50 may repeat blocks 120-128 to periodically determine updated heart failure statuses of patient 4 such as daily, weekly, monthly, yearly, or at any other suitable period. In some examples, the heart failure status of patient 4 may indicate a possibility that patient 4 may experience an adverse medical event within a certain period of time, such as a recurrence of symptoms, acute heart failure decompensation, or other adverse medical events that may require medical intervention such as hospitalization. Processing circuitry then transmits the health status of patient 4 to a remote computer, such as external device 12 (130). In some examples, processing circuitry 50 may transmit the heart failure status of patient 4 to the remote computer each time processing circuitry 50 determines the heart failure status of patient 4. In other examples, processing circuitry 50 may transmit the heart failure status of patient 4 to the remote computer less frequently, such as weekly or at any other suitable interval.

Figure 8:
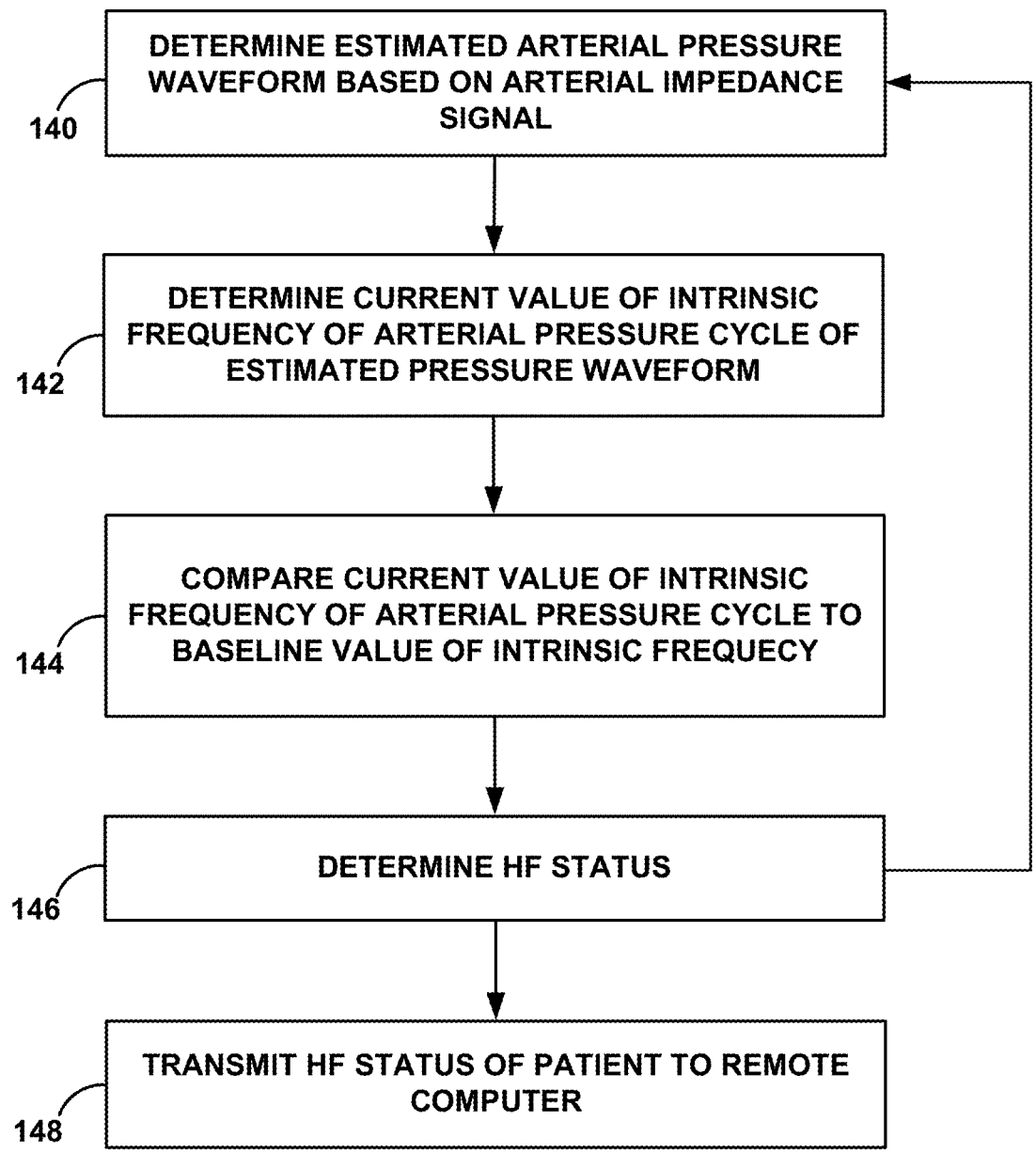
FIG. 8 is a flow diagram illustrating another example technique for determining a heart failure status of a patient based on a comparison of a current value of an intrinsic frequency to a baseline value of the intrinsic frequency and transmitting the heart failure status to a remote computer.

FIG. 8 is a flow diagram illustrating another example technique for determining, by processing circuitry of medical device system 2 (e.g., processing circuitry 50), a heart failure status of patient 4 based on a comparison of a value of at least one current value of an intrinsic frequency of an arterial pressure cycle of patient 4 to a baseline value of the intrinsic frequency, which may be stored in baseline/threshold tables 64 of memory 56. As with FIG. 7, FIG. 8 may be an example of the example technique of FIG. 6. Thus, one or more aspects of the example technique illustrated in FIG. 8 may be substantially similar to one or more aspects of the example techniques illustrated in FIG. 6 and FIG. 7.

The example technique of FIG. 8 may differ from the example technique of FIG. 7 in that processing 50 may determine the heart failure status of patient 4 based on a comparison of at least one current value of the intrinsic frequency of an arterial pressure cycle of patient 4 to at least one corresponding baseline value of the intrinsic frequency. Thus, the technique of FIG. 8 may be used, for example, to monitor changes in an absolute value of the intrinsic frequency occurring over the course of multiple predetermined periods of time. In contrast, in the example technique of FIG. 7, processing circuitry 50 may determine the heart failure status of patient 4 based on a value of a relationship between a value of a first intrinsic frequency of an arterial pressure cycle and a value of a second intrinsic frequency of the arterial pressure cycle. Thus, the technique of FIG. 7 may be used, for example, to monitor changes in at least one of a difference between the value of the first intrinsic frequency and the value of the second intrinsic frequency or a ratio of the value of the first intrinsic frequency to the value of the second intrinsic frequency over the course of multiple predetermined periods of time. In some instances, the example techniques of FIGS. 7 and 8 may be used to monitor different aspects of a heart failure status of patient 4.

According to the example of FIG. 8, processing circuitry 50 determines an estimated arterial pressure waveform of patient 4 based on an arterial impedance signal received from at least two of the plurality of electrodes of IMD 10 (e.g., electrodes 16A, 16B) (140), such as in a manner substantially similar to that described above with respect to (110) of FIG. 6 and/or (120) of FIG. 7. The estimated arterial pressure waveform of patient 4 includes a plurality of arterial pressure cycles and each of the plurality of arterial pressure cycles corresponds to a different cardiac cycle of a plurality of cardiac cycles of patient 4.

After determining the estimated arterial pressure waveform of patient 4, processing circuitry 50 then determines, for at least some of the plurality of cardiac cycles of patient 4, at least one current value of an intrinsic frequency of the corresponding arterial pressure cycle (142), such as in a manner substantially similar to that described above with respect to (112) of FIG. 6. In some examples, the at least one current value of the intrinsic frequency may be a current value of a first intrinsic frequency of a first portion of the arterial pressure cycle (e.g., a portion occurring prior to a dicrotic notch of the corresponding arterial pressure cycle) and/or a current value of a second intrinsic frequency of a second portion of the arterial pressure cycle (e.g., a portion occurring subsequent to a dicrotic notch of the corresponding arterial pressure cycle). In some examples, processing 50 may determine the at least one value of the intrinsic frequency by determining a representative value of the at least one current value of the intrinsic frequency based on at least two values of the intrinsic frequency of at least two corresponding arterial pressure cycles.

After determining the at least one current value of the intrinsic frequency of the corresponding arterial pressure cycle, processing circuitry 50 then compares the at least one current value of the intrinsic frequency to at least one corresponding baseline value of the intrinsic frequency (144). For example, processing circuitry 50 may compare the at least one current value of the intrinsic frequency to the at least one corresponding baseline value of the intrinsic frequency by determining a difference between a current value of the intrinsic frequency and the corresponding baseline value of the intrinsic frequency.

After comparing the at least one current value of the intrinsic frequency to at least one corresponding baseline value of the intrinsic frequency, such as determining the difference between a current value of the intrinsic frequency and the corresponding baseline value of the intrinsic frequency, processing circuitry 50 determines a heart failure status of patient 4 based on the comparison (146). Processing circuitry 50 may determine the heart failure status of patient 4 by determining whether the value of such a difference satisfies at least one corresponding intrinsic frequency threshold value associated with a change in the heart failure status of patient 4, which may be stored in baseline/threshold tables 64 of memory 56.

In some examples, processing circuitry 50 may periodically determine an updated value of the intrinsic frequency threshold. Processing circuitry 50 may determine the updated value of the intrinsic frequency threshold in a manner similar to the manner in which processing circuitry 50 may determine updated values of the intrinsic frequency difference threshold or the intrinsic frequency ratio threshold described above with respect to FIG. 7, such as based on at least one current values of the intrinsic frequency that correspond to one or more previous predetermined periods of time. Periodically determining updated values of the intrinsic frequency threshold may enable processing circuitry 50 to track trends in the current value of the intrinsic frequency of arterial pressure cycles of patient 4 that occur during over the course of multiple predetermined periods of time (e.g., current values of the intrinsic frequency occurring when patient 4 is expected to be asleep or awake).

As with blocks 110-114 of the example of FIG. 6 or blocks 120-128 of the example of FIG. 7, processing circuitry 50 may repeat blocks 140-146 to periodically determine updated heart failure statuses of patient 4 such as daily, weekly, monthly, or at any other suitable period. In some examples, the heart failure status of patient 4 may indicate a possibility that patient 4 may experience an adverse medical event within a certain period of time, such as a recurrence of symptoms, acute heart failure decompensation, or other adverse medical events that may require medical intervention such as hospitalization. Processing circuitry then transmits the health status of patient 4 to a remote computer, such as external device 12 (148). In some examples, processing circuitry 50 may transmit the heart failure status of patient 4 to the remote computer each time processing circuitry 50 determines the heart failure status of patient 4. In other examples, processing circuitry 50 may transmit the heart failure status of patient 4 to the remote computer less frequently, such as weekly or at any other suitable interval.

In any of the example techniques of FIGS. 6-8, processing circuitry 50 may determine the heart failure status of patient 4 based on one or more other physiological parameters that are indicative of the heart failure status of patient 4 in combination with intrinsic frequency of an arterial pressure cycle. For example, processing circuitry 50 may determine the heart failure status of patient 4 based on a plurality of physiological parameters that include at least one value of an intrinsic frequency and a value of a subcutaneous tissue impedance of the patient. In such examples, processing circuitry 50 may determine a value of the subcutaneous tissue impedance of patient 4 based on a subcutaneous tissue impedance signal received from at least two of the plurality of electrodes of IMD 10 (e.g., electrodes 16A, 16B). The at least two of the plurality of electrodes of IMD 10 from which processing circuitry 50 receives the subcutaneous tissue impedance signal may be the same as or different from electrodes 16A, 16B from which processing circuitry 50 receives the arterial impedance signal. Processing circuitry 50 then may determine the heart failure status of patient 4 based on at least one value of an intrinsic frequency metric and the value of the subcutaneous tissue impedance. In some examples, a plurality of physiological parameters may include one or more other physiological parameters, in addition to or instead of subcutaneous tissue impedance, that are indicative of the heart failure status of patient 4 or that more broadly are indicative of a health status of patient 4.

Figure 9:
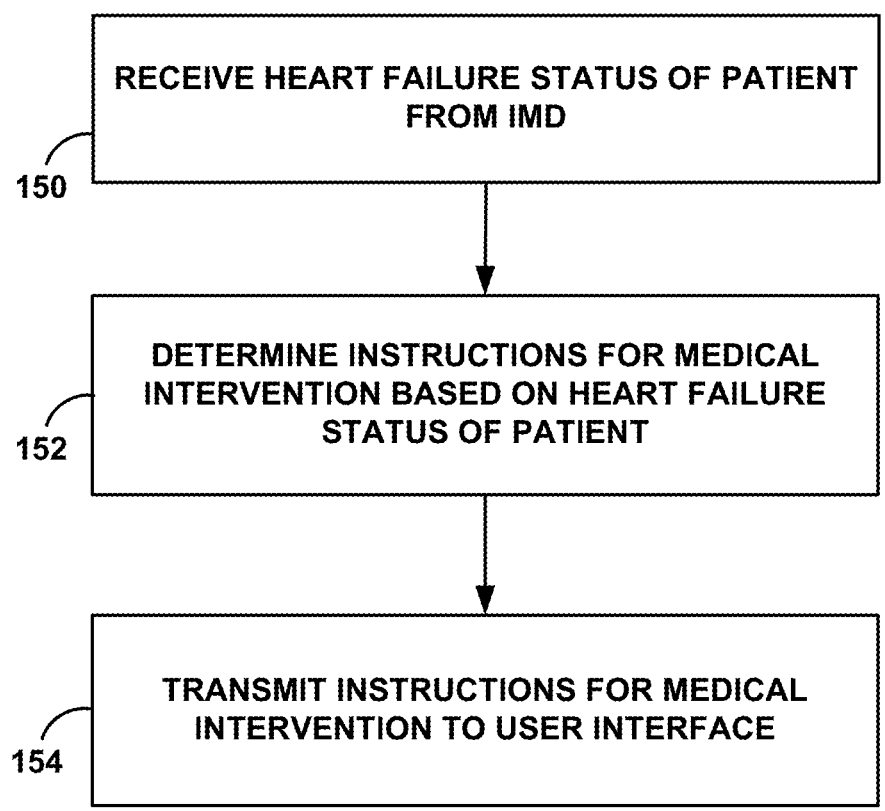
FIG. 9 is a flow diagram illustrating an example technique for a remote computer to determine instructions for a medical intervention based on a heart failure status of a patient received from the leadless implantable medical device of FIG. 1 and transmit the instructions to a user interface.

FIG. 9 is a flow diagram illustrating an example technique for a remote computer (e.g., external device 12) to determine instructions for a medical intervention based on a heart failure status of patient 4 received from IMD 10 and transmit the instructions to a user interface. The method illustrated in FIG. 9 may be used with any of the methods for determining a health status by IMD 10 described herein, such as the methods illustrated in FIGS. 6-8. In some examples, external device 12 is configured to receive a heart failure status of patient 4 from IMD 10, which may be transmitted to a processing circuitry of external device 12 via communication circuitry 54 and antenna 26 of IMD 10 (150). In some examples, the heart failure status of patient 4 may include a possibility that the patient will experience an adverse medical event, such as recurrent symptom(s), acute decompensation, hospitalization, or other adverse medical events.

In some examples, upon receiving the heart failure status of patient 4 from IMD 10 and prior to determining instructions for a medical intervention for patient 4, external device 12 may transmit one or more queries to a user device. For example, external device 12 may ask patient 4, clinician, other medical personnel, or another caregiver to answer questions about recent or current activities or symptoms of patient 4, such as whether patient 4 recently has exercised, taken medications, or experienced symptoms. In addition, external device 12 may interrogate IMD 10 for recently-determined or current values of at least one intrinsic frequency metric of patient 4, differences between first and second values of at least one intrinsic frequency metric of patient 4, differences between current and baseline values of at least one intrinsic frequency of patient 4, and/or heart-failure status determinations pertaining to patient 4, if IMD 10 did not already transmit such values, differences, and/or heart-failure status determinations to external device 12. Based on the heart failure status of patient 4, and optionally based on answers to queries and/or the current values of patient 4, external device 12 then may determine instructions for a medical intervention for patient 4 (152).

External device 12 may determine instructions for one or more medical interventions for patient 4 based on the heart failure status of patient 4. For example, external device 12 may determine instructions for modifying (e.g., start, stop, increase, or decrease) a dose of one or more drugs, such as diuretics, nitrates, beta-blockers, ivabradine, or inotropes. In some examples, instructions for medical interventions for patient 4 may take into account the presence of cardiac arrhythmia, as indicated by ECG signals of patient 4 detected by IMD 10. For example, instructions determined by external device 12 in the presence of arrhythmia may include instructions for patient 4 to avoid taking certain medications, instruct patient 4 to visit a healthcare facility, or may recommend starting CRT or changing CRT parameters.

In some examples, external device 12 may determine the instructions for medical intervention independent of input by a clinician or other medical personnel, such as by selecting among treatment options stored in a memory of external device 12 or a centralized database that are associated with recently-determined or current values of at least one intrinsic frequency metric of patient 4, differences between first and second values of at least one intrinsic frequency metric of patient 4, differences between current and baseline values of at least one intrinsic frequency metric of patient 4, and/or heart-failure status determinations pertaining to patient 4. In other examples, a clinician may determine the instructions for medical intervention on substantially the same basis and input the instructions to external device 12. External device 12 then may transmit the instructions to an interface of the user device with patient 4 (154).

In some examples, external device 12 may transmit follow-up queries to patient 4 or a caregiver via the user device after transmitting the instructions. Such queries may include questions pertaining to patient 4's understanding of the transmitted instructions, whether patient 4 has complied with the instructed medical intervention, and/or whether patient 4 is experiencing symptoms. External device 12 may store patient 4's responses in a memory of external device 12, or in a centralized database. A clinician or other medical personnel may review the responses, and remotely follow-up with patient 4 as needed following any changes to patient 4's treatment for a heart failure condition. In this manner, the techniques and systems described herein advantageously may enable patient 4 to receive individualized, frequently updated treatment at less expense than a comparable number of clinician visits and/or hospitalizations would incur. In addition, the techniques and systems may help reduce recurrence of symptoms, acute decompensation events, and/or cardiac remodeling that may be caused by acute decompensation episodes, which in turn may help reduce or slow the progression of a heart failure condition of patient 4.

Figure 10:
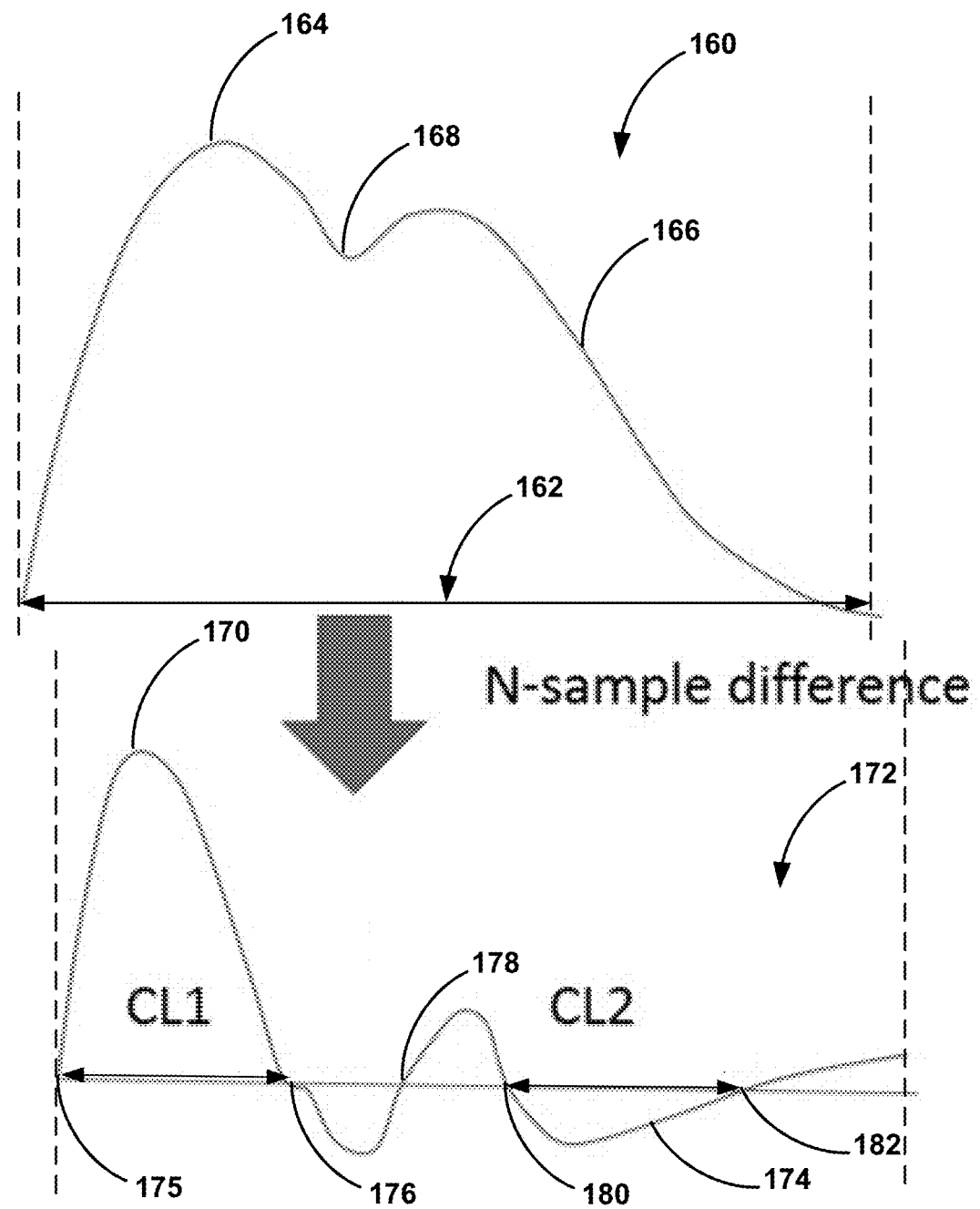
FIG. 10 is a conceptual drawing illustrating example estimated arterial pressure waveforms that each include first and second portions that may be used in an example technique for determining a value of a first intrinsic frequency of a first portion of the corresponding arterial pressure cycle and a value of a second intrinsic frequency of a second portion of the corresponding arterial pressure cycle.

FIG. 10 is a conceptual drawing illustrating a portion of an example estimated arterial waveform 160 that includes an arterial pressure cycle 162 that includes a first portion 164 and a second portion 166. First portion 164 and second portion 166 of arterial pressure cycle 162 may be used in an example technique for determining a value of a first intrinsic frequency of first portion 164 and a value of a second intrinsic frequency of the second portion 166 of arterial pressure cycle 162. First portion 164 of arterial pressure cycle 162 is prior to a dicrotic notch 168 of arterial pressure cycle 162 and second portion 166 of arterial pressure cycle 162 is subsequent to dicrotic notch 168. Arterial pressure cycle 162 may correspond to a cardiac cycle of patient 4.

In examples in which processing circuitry of medical device system 2 (e.g., processing circuitry 50 of IMD 10) determines a value of a first intrinsic frequency of first portion 164 of arterial pressure cycle 162 prior to dicrotic notch 168 ($\omega 1$) and a value of a second intrinsic frequency of second portion 166 of arterial pressure cycle 162 that is subsequent to dicrotic notch 168 ($\omega 2$), processing circuitry 50 may in some examples determine $\omega 1$ based on a determined first cycle length (CL1) of a first portion 170 of a determined differential waveform 172 of estimated arterial pressure waveform 160. Processing circuitry 50 may determine $\omega 2$ based on a determined second cycle length (CL2) of a second portion 174 of differential waveform 172 of estimated arterial pressure waveform 160 that is subsequent to CL1. In some examples, first portion 170 of differential waveform 172 may correspond to first portion 164 of arterial pressure cycle 162 of estimated arterial pressure waveform 160 and/or to a first portion of a cardiac cycle corresponding to arterial pressure cycle 162. Second portion 174 of differential waveform 172 may correspond to second portion 166 of arterial pressure cycle 162 and/or to a second portion of the cardiac cycle corresponding to arterial pressure cycle 162.

Processing circuitry 50 may determine differential waveform 172 of estimated arterial pressure waveform 160. For example, processing circuitry 50 may, for each sample (i) of estimated arterial pressure waveform 160, determine a corresponding sample of the differential waveform 172 according to the following equation: differential sample(i)=sample(i)−sample (i-N), where N is an integer greater than or equal to 1. Processing circuitry 50 may determine CL1 and CL2 by identifying respective zero crossings of differential waveform 172. In some examples, zero crossings of differential waveform 172 may correspond to respective portions (e.g., peaks and bottoms) of an atrial waveform.

For example, CL1 may be an interval from a first positive-going zero crossing 175 to a first negative-going zero crossing 176 of differential waveform 172 during the cardiac cycle corresponding to arterial pressure cycle 162. First positive-going zero crossing 175 and first negative-going zero crossing 176 may be measured form a suitable fiducial point (e.g., from an R-wave and/or any other suitable fiducial), as may be subsequent zero crossings. CL2 may be an interval subsequent to a second positive-going zero crossing 178 of differential waveform 172 during the cardiac cycle corresponding to arterial pressure cycle 162. For example, CL2 may be an interval from a second negative-going zero crossing 180 to a third positive-going zero crossing 182. In such examples, processing circuitry 50 may determine that dicrotic notch 168 of arterial pressure cycle 162 occurs at second positive-going zero crossing 178. In some examples, processing circuitry 50 may identify zero-crossings 175, 176, 178, 180, and 182 where the product of adjacent samples of differential waveform 172 is negative and the difference between the adjacent samples satisfies, e.g., is greater than, a threshold such that zero-crossings 175, 176, 178, 180, and 182 may be considered "significant" zero crossings. Whether a zero-crossing is positive or negative may be determined based on the sign of the latter of the adjacent samples.

In such examples, $\omega 1$ is proportional to 1/CL1, and $\omega 2$ is proportional to 1/CL2. Consequently, in some examples, processing circuitry 50 may use 1/CL1 and/or 1/CL2 in any of the techniques of the disclosure in place of (or in addition to) the corresponding one of $\omega 1$ and/or $\omega 2$. In some examples, processing circuitry 50 may choose multiple scales for N of an N-sample difference, which may allow for CL in the known ranges for $\omega 1$ and $\omega 2$ and may then average the CL at different scales. In other examples, processing circuitry 50 may choose a fixed N that may enable estimation of CL in the known ranges for $\omega 1$ and $\omega 2$.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the terms "processor" or "processing circuitry" as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:

1. A method for determining a heart failure status of a patient using a medical device comprising a plurality of electrodes, the method comprising, by processing circuitry of a medical device system comprising the medical device:

determining an estimated arterial pressure waveform of the patient based on an arterial impedance signal received from at least two of the plurality of electrodes, wherein the estimated arterial pressure waveform comprises a plurality of arterial pressure cycles and wherein each of the plurality of arterial pressure cycles corresponds to a different cardiac cycle of a plurality of cardiac cycles of the patient;

determining, for at least some of the plurality of cardiac cycles, at least one value of an intrinsic frequency of the corresponding arterial pressure cycle;

determining the heart failure status of the patient based on the at least one value of the intrinsic frequency; and further comprising, by the processing circuitry:

transmitting the heart failure status of the patient to a remote computer; and receiving, from the remote computer, instructions for a medical intervention based on the heart failure status of the patient.

2. The method of claim 1, wherein the instructions for the medical intervention comprise at least one of a change in a drug selection, a change in a drug dosage, instructions to schedule a visit with a clinician, or instructions for the patient to seek medical attention.

3. The method of claim 1, further comprising, in response to a worsening of the heart failure status presenting, by the remote computer, a graphical user interface indicating the worsening of the heart failure status.

4. A method for determining a heart failure status of a patient using a medical device comprising a plurality of electrodes, the method comprising, by processing circuitry of a medical device system comprising the medical device:

determining an estimated arterial pressure waveform of the patient based on an arterial impedance signal received from at least two of the plurality of electrodes, wherein the estimated arterial pressure waveform comprises a plurality of arterial pressure cycles and wherein each of the plurality of arterial pressure cycles corresponds to a different cardiac cycle of a plurality of cardiac cycles of the patient;

determining, for at least some of the plurality of cardiac cycles, at least one value of an intrinsic frequency of the corresponding arterial pressure cycle;

determining the heart failure status of the patient based on the at least one value of the intrinsic frequency; and further comprising, by the processing circuitry:

transmitting the heart failure status of the patient to a remote computer;

receiving, from the remote computer, instructions for a medical intervention based on the heart failure status of the patient; and transmitting the instructions for the medical intervention to a user interface.

5. A method for determining a heart failure status of a patient using a medical device comprising a plurality of electrodes, the method comprising, by processing circuitry of a medical device system comprising the medical device:

determining an estimated arterial pressure waveform of the patient based on an arterial impedance signal received from at least two of the plurality of electrodes, wherein the estimated arterial pressure waveform comprises a plurality of arterial pressure cycles and wherein each of the plurality of arterial pressure cycles corresponds to a different cardiac cycle of a plurality of cardiac cycles of the patient;

determining, for at least some of the plurality of cardiac cycles, at least one value of an intrinsic frequency of the corresponding arterial pressure cycle; and determining the heart failure status of the patient based on the at least one value of the intrinsic frequency;

wherein the medical device is an implantable medical device configured for implantation within the patient; and wherein the implantable medical device comprises a housing, wherein the at the least two of the plurality of electrodes are positioned on the housing, and wherein the housing is configured for implantation within the patient such that the at least two of the plurality of electrodes are substantially aligned with a longitudinal axis of an artery of the patient.

6. A method for determining a heart failure status of a patient using a medical device comprising a plurality of electrodes, the method comprising, by processing circuitry of a medical device system comprising the medical device:

determining an estimated arterial pressure waveform of the patient based on an arterial impedance signal received from at least two of the plurality of electrodes, wherein the estimated arterial pressure waveform comprises a plurality of arterial pressure cycles and wherein each of the plurality of arterial pressure cycles corresponds to a different cardiac cycle of a plurality of cardiac cycles of the patient;

determining, for at least some of the plurality of cardiac cycles, at least one value of an intrinsic frequency of the corresponding arterial pressure cycle; and determining the heart failure status of the patient based on the at least one value of the intrinsic frequency;

wherein the medical device is an implantable medical device configured for implantation within the patient; and wherein the implantable medical device comprises a leadless implantable medical device.

7. The method of claim 1 or claim 4 or claim 5 or claim 6, wherein the medical device system further comprises a medical device configured to deliver cardiac pacing to the patient, the method further comprising:

determining a value of at least one pacing parameter based on the at least one value of the intrinsic frequency; and controlling the medical device to deliver the cardiac pacing at the determined value of the at least one pacing parameter.

8. The method of claim 7, wherein the at least one pacing parameter comprises at least one cardiac resynchronization therapy (CRT) parameter, and wherein controlling the medical device to deliver the cardiac pacing at the value of the at least one pacing parameter comprises controlling the medical device to provide CRT.

9. A system for determining a heart failure status of a patient using a medical device comprising a plurality of electrodes, the system comprising:

the medical device, wherein the medical device comprises one or more sensors; and processing circuitry configured to:

determine an estimated arterial pressure waveform of the patient based on an arterial impedance signal received from at least two of the plurality of electrodes, wherein the estimated arterial pressure waveform comprises a plurality of arterial pressure cycles and wherein each of the plurality of arterial pressure cycles corresponds to a different cardiac cycle of a plurality of cardiac cycles of the patient;

determine, for at least some of the plurality of cardiac cycles, at least one value of an intrinsic frequency of the corresponding arterial pressure cycle; and determine the heart failure status of the patient based on the at least one value of the intrinsic frequency;
wherein the processing circuitry is further configured to:
transmit the heart failure status of the patient to a remote computer; and
receive, from the remote computer, instructions for a medical intervention based on the heart failure status of the patient.

10. The system of claim 9, wherein the instructions for the medical intervention comprise at least one of a change in a drug selection, a change in a drug dosage, instructions to schedule a visit with a clinician, or instructions for the patient to seek medical attention.

11. The system of claim 9, further comprising the remote computer, wherein, in response to a worsening of the heart failure status the remote computer is configured to present a graphical user interface indicating the worsening of the heart failure status.

12. A system for determining a heart failure status of a patient using a medical device comprising a plurality of electrodes, the system comprising:
the medical device, wherein the medical device comprises one or more sensors; and
processing circuitry configured to:
determine an estimated arterial pressure waveform of the patient based on an arterial impedance signal received from at least two of the plurality of electrodes, wherein the estimated arterial pressure waveform comprises a plurality of arterial pressure cycles and wherein each of the plurality of arterial pressure cycles corresponds to a different cardiac cycle of a plurality of cardiac cycles of the patient;
determine, for at least some of the plurality of cardiac cycles, at least one value of an intrinsic frequency of the corresponding arterial pressure cycle; and
determine the heart failure status of the patient based on the at least one value of the intrinsic frequency; and
wherein the processing circuitry is further configured to:
transmit the heart failure status of the patient to a remote computer;
receive, from the remote computer, instructions for a medical intervention based on the heart failure status of the patient; and
transmit the instructions for the medical intervention to a user interface.

13. A system for determining a heart failure status of a patient using a medical device comprising a plurality of electrodes, the system comprising:
the medical device, wherein the medical device comprises one or more sensors; and
processing circuitry configured to:
determine an estimated arterial pressure waveform of the patient based on an arterial impedance signal received from at least two of the plurality of electrodes, wherein the estimated arterial pressure waveform comprises a plurality of arterial pressure cycles and wherein each of the plurality of arterial pressure cycles corresponds to a different cardiac cycle of a plurality of cardiac cycles of the patient;
determine, for at least some of the plurality of cardiac cycles, at least one value of an intrinsic frequency of the corresponding arterial pressure cycle; and
determine the heart failure status of the patient based on the at least one value of the intrinsic frequency;
wherein the medical device is an implantable medical device configured for implantation within the patient; and
wherein the implantable medical device comprises a housing, wherein the at the least two of the plurality of electrodes are positioned on the housing, and wherein the housing is configured for implantation within the patient such that the at least two of the plurality of electrodes are substantially aligned with a longitudinal axis of an artery of the patient.

14. A system for determining a heart failure status of a patient using a medical device comprising a plurality of electrodes, the system comprising:
the medical device, wherein the medical device comprises one or more sensors; and
processing circuitry configured to:
determine an estimated arterial pressure waveform of the patient based on an arterial impedance signal received from at least two of the plurality of electrodes, wherein the estimated arterial pressure waveform comprises a plurality of arterial pressure cycles and wherein each of the plurality of arterial pressure cycles corresponds to a different cardiac cycle of a plurality of cardiac cycles of the patient;
determine, for at least some of the plurality of cardiac cycles, at least one value of an intrinsic frequency of the corresponding arterial pressure cycle; and
determine the heart failure status of the patient based on the at least one value of the intrinsic frequency;
wherein the medical device is an implantable medical device configured for implantation within the patient; and
wherein the implantable medical device comprises a leadless implantable medical device.

15. The system of claim 9 or claim 12 or claim 13 or claim 14,
wherein the medical device system further comprises a medical device configured to deliver cardiac pacing to the patient, and wherein the processing circuitry is further configured to:
determine a value of at least one pacing parameter based on the at least one value of the intrinsic frequency; and
control the medical device to deliver the cardiac pacing at the determined value of the at least one pacing parameter.

16. The system of claim 15, wherein the at least one pacing parameter comprises at least one cardiac resynchronization therapy (CRT) parameter, and wherein the processing circuitry is configured to control the medical device to deliver the cardiac pacing at the value of the at least one pacing parameter by at least controlling the medical device to provide CRT.

* * * * *